(12) United States Patent
Kaar et al.

(10) Patent No.: US 11,535,840 B2
(45) Date of Patent: Dec. 27, 2022

(54) METHOD FOR RECYCLABLY USING AN ENZYME

(71) Applicants: THE REGENTS OF THE UNIVERSITY OF COLORADO, Denver, CO (US); THE UNIVERSITY OF CHICAGO, Chicago, IL (US)

(72) Inventors: Joel L. Kaar, Lafayette, CO (US); Garrett Chado, San Francisco, CA (US); Mark Stoykovich, Chicago, IL (US)

(73) Assignees: The Regents of the University of Colorado, a body corporate, Denver, CO (US); The University of Chicago, Chicago, IL (US)

( * ) Notice: Subject to any disclaimer, the term of this patent is extended or adjusted under 35 U.S.C. 154(b) by 0 days.

(21) Appl. No.: 17/284,186

(22) PCT Filed: Oct. 9, 2019

(86) PCT No.: PCT/US2019/055416
§ 371 (c)(1),
(2) Date: Apr. 9, 2021

(87) PCT Pub. No.: WO2020/076963
PCT Pub. Date: Apr. 16, 2020

(65) Prior Publication Data
US 2021/0332346 A1 Oct. 28, 2021

Related U.S. Application Data

(60) Provisional application No. 62/744,075, filed on Oct. 10, 2018.

(51) Int. Cl.
*C12N 9/96* (2006.01)

(52) U.S. Cl.
CPC ..................... *C12N 9/96* (2013.01)

(58) Field of Classification Search
None
See application file for complete search history.

(56) References Cited

U.S. PATENT DOCUMENTS

| | | |
|---|---|---|
| 6,433,078 B1 | 8/2002 | Gololobov et al. |
| 2007/0123646 A1 | 5/2007 | Lele et al. |
| 2016/0101190 A1 | 4/2016 | Russell et al. |
| 2018/0051271 A1 | 2/2018 | Russell et al. |
| 2021/0332346 A1* | 10/2021 | Kaar .................. C12N 9/20 |

FOREIGN PATENT DOCUMENTS

| | | |
|---|---|---|
| CN | 103468768 | 12/2013 |
| WO | WO 2020/076963 | 4/2020 |

OTHER PUBLICATIONS

Kobayashi (Proc. Jpn. Acad. Ser. B, v.86 (2010), pp. 338-365).*
Kobayashi (Biomacromolecules, 2000, 1 (1):3-5, Abstract only).*
Akbar et al., "Direct solubilization of enzyme aggregates with enhanced activity in nonaqueous media," Biotechnology and Bioengineering, vol. 96, No. 6, Apr. 15, 2007, pp. 1030-1039.
Asai et al., "Structural Study on the UCST-Type Phase Separation of Poly(N-isopropylacrylamide) in Ionic Liquid," Macromolecules, vol. 46, No. 3, Jan. 31, 2013, pp. 1101-1106.
Behr et al., "Thermoregulated Liquid/Liquid Catalyst Separation and Recycling," Advanced Synthesis & Catalysis, vol. 348, No. 12-13, Aug. 2006, pp. 1485-1495.
Brogan et al., "Non-aqueous homogenous biocatalytic conversion of polysaccharides in ionic liquids using chemically modified glucosidase," Nature Chemistry, vol. 10, Jun. 25, 2018, pp. 859-865.
Brogan et al., "Solubilizing and Stabilizing Proteins in Anhydrous Ionic Liquids through Formation of Protein-Polymer Surfactant Nanoconstructs," Journal of the American Chemical Society, vol. 138, No. 13, Mar. 14, 2016, pp. 4494-4501.
Bulmus et al., "Site-Specific Polymer-Streptavidin Bioconjugate for pH-Controlled Binding and Triggered Release of Biotin," Bioconjugate Chemistry, vol. 11, No. 1, Dec. 3, 1999, pp. 78-83.
Chado et al., "Modification of Lipase with Poly(4-acryloylmorpholine) Enhances Solubility and Transesterification Activity in Anhydrous Ionic Liquids," Biomacromolecules, vol. 19, No. 4, Mar. 9, 2018, pp. 1324-1332.
Chen et al., "Effects of polyelectrolyte complexation on the UCST of zwitterionic polymer," Polymer, vol. 41, No. 1, Jan. 2000, pp. 141-147.
Cobo et al., "Smart hybrid materials by conjugation of responsive polymers to biomacromolecules," Nature Materials, vol. 14, Nov. 17, 2014, pp. 143-159.
Cummings et al., "Polymer-Based Protein Engineering Enables Molecular Dissolution of Chymotrypsin in Acetonitrile," ACS Macro Letters, vol. 5, No. 4, Mar. 30, 2016, pp. 493-497.
Cummings et al., "Tailoring enzyme activity and stability using polymer-based protein engineering," Biomaterials, vol. 34, No. 30, Oct. 2013, pp. 7437-7443.
De et al., "Temperature-Regulated Activity of Responsive Polymer-Protein Conjugates Prepared by Grafting-from via RAFT Polymerization," Journal of the American Chemical Society, vol. 130, No. 34, Jul. 30, 2008, pp. 11288-11289.
Depp et al., "Enzyme Sheathing Enables Nanoscale Solubilization of Biocatalyst and Dramatically Increases Activity in Organic Solvent," Biomacromolecules, vol. 9, No. 4, Feb. 23, 2008, pp. 1348-1351.

(Continued)

*Primary Examiner* — Hope A Robinson
(74) *Attorney, Agent, or Firm* — Sheridan Ross P.C.

(57) ABSTRACT

The invention provides methods and systems by which enzymes can be modified to improve solubility, catalytic activity, recoverability, and recyclability. The enzyme may be modified with a thermosensitive copolymer to form an enzyme-polymer conjugate that exhibits upper critical solution temperature (UCST) and/or lower critical solution temperature (LCST)-type behavior in an organic solvent, ionic liquid, or other solvent. Methods and systems of the invention facilitate the use of enzymes as biocatalysts in solvents.

11 Claims, 6 Drawing Sheets

(56) References Cited

OTHER PUBLICATIONS

Dong et al., "Three-Dimensional Ordered Antibody Arrays Through Self-Assembly of Antibody-Polymer Conjugates," vol. 56, No. 5, Jan. 24, 2017, pp. 1273-1277.

Grazu et al., "Promotion of multipoint covalent immobilization through different regions of genetically modified penicillin G acylase from E. coli," Process Biochemistry, vol. 45, No. 3, Mar. 2010, pp. 390-398.

Hoffman et al., "Conjugates of stimuli-responsive polymers and proteins," Progress in Polymer Science, vol. 32, No. 8-9, Aug. 2007, pp. 922-932.

Jin et al., "Thermoregulated phase transfer ligands and catalysis. I. Synthesis of novel polyether-substituted triphyenylphosphines and application of their rhodium complexes in two-phase hydroformylation," Journal of Molecular Catalysis A: Chemical, vol. 116, No. 1-2, Feb. 24, 1997, pp. 55-58.

Lam et al., "The Nature of Protein Interactions Governing Globular Protein-Polymer Block Copolymer Self-Assembly," Biomacromolecules, vol. 15, No. 4, Mar. 21, 2014, pp. 1248-1258.

Limadinata et al., "Temperature-responsive nanobiocatalysts with an upper critical solution temperature for high performance biotransformation and easy catalyst recycling: efficient hydrolysis of cellulose to glucose," Green Chemistry, vol. 17, No. 2, 2015, pp. 1194-1203.

Liu et al., "Preparation of biodegradable and thermoresponsive enzyme-polymer conjugates with controllable bioactivity via RAFT polymerization," European Polymer Journal, vol. 49, No. 10, Oct. 2013, pp. 2949-2960.

Liu et al., "Thermoregulated phase transfer ligands and catalysis XVIII: synthesis of N,N-dipolyoxyethylene-substituted-2-(diphenylphosphino)phenylamine (PEO-DPPPA) and the catalytic activity of its rhodium complex in the aqueous-organic biphasic hydroformylation of 1-decene," Journal of Molecular Catalysis A: Chemical, vol. 198, No. 1-2, May 1, 2003, pp. 23-27.

Lou et al., "Covalently immobilized lipase on a thermoresponsive polymer with an upper critical solution temperature as an efficient and recyclable asymmetric catalyst in aqueous media," ChemCatChem, vol. 10, No. 5, 2018, pp. 1166-1172.

Mackenzie et al., "Recyclable Thermoresponsive Polymer-Cellulase Bioconjugates for Biomass Depolymerization," Journal of the American Chemical Society, vol. 135, No. 1, Jan. 9, 2013, pp. 293-300.

Murata et al., "Polymer-Based Protein Engineering Can Rationally Tune Enzyme Activity, pH-Dependence, and Stability," Biomacromolecules, vol. 14, No. 6, Apr. 22, 2013, pp. 1919-1926.

Niskanen et al., "How to manipulate the upper critical solution temperature (UCST)?," Polymer Chemistry, vol. 8, Oct. 21, 2016, pp. 220-232.

Obermeyer et al., "Synthesis and Application of Protein-Containing Block Copolymers," ACS Macro Letters, vol. 4, No. 1, Jan. 5, 2015, pp. 101-110.

Pace et al., "Protein structure, stability and solubility in water and other solvents," Philosophical Transactions of the Royal Society B: Biological Sciences, vol. 359, Jul. 2004, pp. 1225-1235.

Panganiban et al., "Random heteropolymers preserve protein function in foreign environments," Science, vol. 359, No. 6381, Mar. 16, 2018, pp. 1239-1243.

Panza et al., "Fluorinated NAD as an affinity surfactant," Chemical Communications, vol. 9, Apr. 8, 2002, pp. 928-929.

Rodrigues et al., "Modifying enzyme activity and selectivity by immobilization," Chemical Society Reviews, vol. 42, 2013, pp. 6290-6307.

Seuring et al., "First Example of a Universal and Cost-Effective Approach: Polymers with Tunable Upper Critical Solution Temperature in Water and Electrolyte Solution," Macromolecules, vol. 45, No. 9, Apr. 26, 2012, pp. 3910-3918.

Seuring et al., "Polymers with Upper Critical Solution Temperature in Aqueous Solution," Macro-Molecular Rapid Communications, vol. 33, No. 22, Nov. 23, 2012, pp. 1898-1920.

Sheldon, "Enzyme Immobilization: The Quest for Optimum Performance," Advanced Synthesis & Catalysis, vol. 349, 2007, pp. 1289-1307.

Shimoboji et al., "Photoresponsive polymer-enzyme switches," Proceedings of the National Academy of Sciences of the United States of America, vol. 99, No. 26, Dec. 24, 2002, pp. 16592-16596.

Shimoboji et al., "Photoswitching of Ligand Association with a Photoresponsive Polymer-Protein Conjugate," Bioconjugate Chemistry, vol. 13, No. 5, Jul. 19, 2002, pp. 915-919.

Tischer et al. "Immobilized enzymes: crystals or carriers?," Trends in Biotechnology, vol. 17, No. 8, Aug. 1, 1999, pp. 326-335.

Ueki et al., "UCST Phase Transition of Azobenzene-Containing Random Copolymer in an Ionic Liquid," Macromolecules, vol. 44, No. 17, Aug. 15, 2011, pp. 6908-6914.

Ueki, "Stimuli-responsive polymers in ionic liquids," Polymer Journal, vol. 46, May 28, 2014, pp. 646-655.

Wu et al., "A general method for synthesizing enzyme-polymer conjugates in reverse emulsions using Pluronic as a reactive surfactant," Chemical Communications, vol. 51, No. 47, May 5, 2015, pp. 9674-9677.

Zhang et al., "Chemo-enzymatic synthesis of valrubicin using Pluronic conjugated lipase with temperature responsiveness in organic media," RSC Advances, vol. 3, No. 45, Oct. 3, 2013, pp. 22963-22966.

Zhao et al., "Methods for stabilizing and activating enzymes in ionic liquids—A review," Journal of Chemical Technology & Biotechnology, vol. 85, No. 7, Jul. 2010, pp. 891-907.

Zheng et al., "Thermoregulated phase transfer ligands and catalysis. III. Aqueous/organic two-phase hydroformylation of higher olefins by thermoregulated phase-transfer catalysis," Catalysis Today, vol. 44, No. 1-4, Sep. 30, 1998, pp. 175-182.

Zhu et al., "Temperature-responsive enzyme-polymer nanoconjugates with enhanced catalytic activities in organic media," Chemical Communications, vol. 49, May 21, 2013, pp. 6090-6092.

International Search Report prepared by the United States Patent Office dated Dec. 2, 2019, for International Application No. PCT/US2019/055416, 3 pages.

Written Opinion prepared by the United States Patent Office dated Dec. 2, 2019, for International Application No. PCT/US2019/055416, 7 pages.

* cited by examiner

METHOD FOR RECYCLABLY USING AN ENZYME

CROSS-REFERENCE TO RELATED APPLICATION

This application is a national stage application under 35 U.S.C. § 371 and claims the benefit of PCT Application No. PCT/US2019/055416 having an international filing date of 9 Oct. 2019, which designated the United States, and which PCT application claimed the benefit of priority under 35 U.S.C. § 119(e) to U.S. Provisional Patent Application No. 62/744,075, filed 10 Oct. 2018. The entireties of each of the above-referenced applications are incorporated herein by reference.

STATEMENT REGARDING FEDERALLY SPONSORED RESEARCH

This invention was made with government support under grant numbers CBET1454379 and DGE1144083 awarded by the National Science Foundation. The government has certain rights in the invention.

FIELD OF THE INVENTION

The invention relates generally to the use of enzymes as biocatalysts in solvents, and particularly to modified enzymes having improved solubility, catalytic activity, recoverability, and/or recyclability, and methods of making and using such enzymes.

BACKGROUND OF THE INVENTION

In recent years, the use of enzymes as catalysts in industrial-scale chemical processes has become increasingly widespread. Because the preparation and purification of catalysts can be costly, enzymes are typically used as heterogeneous catalysts to facilitate their separation and recycling. One approach for using enzymes as heterogeneous catalysts is immobilization of the enzyme on a solid support, such as a particle or resin, which may also stabilize the enzyme against chemical and/or thermal denaturation. However, while immobilization may improve the recyclability of the enzyme, the attachment of the enzyme to a solid support often has a severe negative effect on the enzyme's catalytic activity; by way of non-limiting example, the activity of an immobilized enzyme may be significantly affected by reduced active site accessibility and mass transfer and diffusional limitations. Furthermore, the cost of producing these supported enzymes may be prohibitive.

SUMMARY OF THE INVENTION

There is a need in the art for systems and methods by which the benefits of both heterogeneous and homogeneous biocatalysis by enzymes may be simultaneously exploited, particularly by reversible dissolution and precipitation of the enzyme in a solvent. It is particularly advantageous for such systems and methods to be suitable for use in a wide range of solvents, including but not limited to organic solvents and ionic liquids, and to preserve the chemical and structural integrity and catalytic activity of the enzyme over many dissolution/precipitation cycles.

It is one aspect of the present invention to provide a method for recyclably using an enzyme as a catalyst in a solvent, comprising a) reacting the enzyme with a polymer to form an enzyme-polymer conjugate; b) dissolving the enzyme-polymer conjugate in the solvent to form a solution; c) performing a chemical reaction in the solution, wherein the enzyme-polymer conjugate catalyzes the chemical reaction; and d) extracting the enzyme-polymer conjugate from the solution, wherein a catalytic activity of the enzyme-polymer conjugate after step d) is at least about 75% of a catalytic activity of the enzyme-polymer conjugate before step c).

The enzyme may, by way of non-limiting example, comprise an oxidoreductase, e.g. an alcohol oxidoreductase, an aldehyde/oxo oxidoreductase, a CH—CH oxidoreductase, a CH—$NH_2$ oxidoreductase (such as an amino acid oxidoreductase), a CH—NH oxidoreductase, an NADH or NADPH oxidoreductase, a nitrogenous donor oxidoreductase, a sulfur oxidoreductase, a diphenol family oxidoreductase, a peroxidase, a monooxygenase, or a dioxygenase (such as a steroid hydroxylase); a transferase, e.g. a one carbon transferase, an aldehyde-ketone transferase, an acyltransferase, a glycosyltransferase, an alkyl or aryl transferase, a nitrogenous transferase, a phosphorous-containing transferase, a sulfur-containing transferase, or a selenium-containing transferase; a hydrolase, e.g. an esterase, a sugar hydrolase, an ether bond hydrolase, a protease, a carbon-nitrogen non-peptide hydrolase, an acid anhydride hydrolase, or a carbon-carbon hydrolase; a lyase, e.g. a carbon-carbon lyase, a carbon-oxygen lyase (such as a dehydratase), a carbon-nitrogen lyase, a carbon-sulfur lyase, a carbon-halide lyase, or a phosphorus-oxygen lyase; an isomerase, e.g. an epimerase or racemase, a geometric isomerase, an intramolecular oxidoreductase, a mutase, an intramolecular lyase, or a topoisomerase; a ligase, e.g. a carbon-oxygen ligase, a carbon-sulfur ligase, a carbon-nitrogen ligase, a carbon-carbon ligase, or a phosphoric ester or nitrogen-metal ligase; or a translocase. In embodiments, the enzyme may be lipase.

The solvent can be an aqueous solvent or a non-aqueous solvent. The solvent may, by way of non-limiting example, comprise an alcohol, e.g. tert-amyl alcohol, benzyl alcohol, 1,4-butanediol, 1,2,4-butanetriol, butanol (such as 2-butanol, N-butanol, or tert-butanol), di(propylene glycol) methyl ether, diethylene glycol, ethanol, ethylene glycol, 2-ethylhexanol, furfuryl alcohol, glycerol, isobutanol, isopropyl alcohol, methanol, 2-(2-methoxyethoxy)ethanol, 2-methyl-1-butanol, 2-methyl-1-pentanol, 3-methyl-2-butanol, neopentyl alcohol, 2-pentanol, 1,3-propanediol, 1-propanol, propylene glycol, or propylene glycol methyl ether; an amide, e.g. dimethylacetamide, dimethylformamide, formamide, N-formylmorpholine, N-methyl-2-pyrrolidone, N-methylformamide, 2-pyrrolidone, tetramethylurea, N-vinylacetamide, or N-vinylpyrrolidone; an amine, e.g. collidine, diethylenetriamine, ethylenediamine, morpholine, piperidine, pyridine, pyrrolidine, quinoline, tetrahydroquinoline, or tributylamine; an aromatic solvent, e.g. benzene, benzonitrile, benzyl alcohol, chlorobenzene, dibenzyl ether, 1,2-dichlorobenzene, 1,2-difluorobenzene, hexafluorobenzene, mesitylene, nitrobenzene, pyridine, tetralin, toluene, 1,2,4-trichlorobenzene, trifluorotoluene, or xylene; an ester, e.g. benzyl benzoate, bis(2-ethylhexyl) adipate, bis(2-ethylhexyl) phthalate, 2-butoxyethanol acetate, butyl acetate (such as sec-butyl acetate or tert-butyl acetate), diethyl carbonate, dimethyl adipate, dioctyl terephthalate, ethyl acetate, ethyl acetoacetate, ethyl butyrate, ethyl lactate, ethylene carbonate, hexyl acetate, isoamyl acetate, isobutyl acetate, isopropyl acetate, methyl acetate, methyl lactate, methyl phenylacetate, methyl propionate, propyl acetate, propylene carbonate, or triacetin; an ether, e.g. tert-amyl ethyl ether, cyclopentyl methyl ether, di-tert-butyl ether, di(propylene glycol) methyl ether, dibutyl ether, diethyl ether, diisopropyl ether, dimethoxyethane, dimethoxymethane, 1,4-dioxane, ethyl tert-butyl ether, methoxyethane, 2-(2-methoxyethoxy)ethanol, methyl tert-butyl ether, 2-methyltetrahydrofuran, morpholine, polyethylene glycol, propylene glycol methyl ether, tetrahydrofuran, tetrahydrofuryl alcohol, tetrahydropyran, or 2,2,5,5-tetramethyltetrahydrofuran; a halogenated solvent, e.g. benzotrichloride, bromoform, bromomethane, carbon tetrachloride, 2-chloro-1,1,1-trifluoroethane, chlorobenzene, chloroform, chloromethane, 1,1-dichloro-1-fluoroethane, 1,2-dichlorobenzene, 1,1-dichloroethane, 1,2-dichloroethane, 1,1-dichloroethene, 1,2-dichloroethene, dichloromethane, 1,2-difluorobenzene, 1,2-diiodoethylene, diiodomethane, FC-75, hexachlorobutadiene, hexafluoro-2-propanol, parachlorobenzotrifluoride, perfluoro-1,3-dimethylcyclohexane, perfluorocyclohexane, perfluorodecalin, perfluorohexane, perfluoromethylcyclohexane, perfluoromethyldecalin, perfluorooctane, perfluorotoluene, perfluorotripentylamine, tetrabromomethane, 1,1,1,2-tetrachloroethane, 1,1,2,2-tetrachloroethane, tetrachloroethylene, 1,2,4-trichlorobenzene, 1,1,1-trichloroethane, 1,1,2-trichloroethane, trichloroethylene, 1,2,3-trichloropropane, 2,2,2-trifluoroethanol, or trifluorotoluene; a hydrocarbon, e.g. benzene, cycloheptane, cyclohexane, cyclohexene, cyclooxtane, cyclopentane, decalin, diesel fuel, dodecane, durene, heptane, hexane, kerosene, ligroin, limonene, mesitylene, methylcyclohexane, naphtha, Nujol, octadecene, pentamethylbenzene, pentane, petroleum benzine, petroleum ether, toluene, tridecane, turpentine, white spirit, or xylene; an inorganic solvent, e.g. ammonia, carbon dioxide, carbon disulfide, carbon tetrachloride, hydrogen fluoride, a molten salt, phosphorus tribromide, sulfur dioxide, sulfuric acid, sulfuryl chloride fluoride, or water; an ionic liquid, e.g. Aliquat 336, 1-butyl-3-methylimidazolium hexafluorophosphate, 1-butyl-3-methylimidazolium tetrachloroferrate, a deep eutectic solvent, 1-ethyl-3-methylimidazolium chloride, ethylammonium nitrate, fluoroantimonic acid, methylpridinium, a molten salt, or trioctylmethylammonium bis(trifluoromethylsulfonyl)imide; a ketone, e.g. acetone, acetophenone, butanone, cyclopentanone, ethyl isopropyl ketone, 2-hexanone, isophorone, β-isophorone, mesityl oxide, methyl isobutyl ketone, methyl isopropyl ketone, 3-methyl-2-pentanone, 2-pentanone, or 3-pentanone; or a nitro solvent, e.g. nitrobenzene, nitroethane, nitromethane, 1-nitropropane, or 2-nitropropane. In embodiments, the solvent may be 1-butyl-3-methylimidazolium hexafluorophosphate.

Both the enzyme and the solvent can be determined based on the reaction utilizing the enzyme. Thus, while efforts have been made by to include several potential solvents and enzymes, one skilled in the art would understand that other enzymes and solvents can be used with this invention, without deviating from the invention.

In embodiments, the method may further comprise purifying the enzyme-polymer conjugate. The enzyme-polymer conjugate may, but need not, be purified by a method selected from the group consisting of affinity chromatography, ammonium sulfate precipitation, dialysis, and size exclusion chromatography.

In embodiments, the polymer may be a copolymer. The polymer may be an alternating copolymer, a block copolymer, a gradient copolymer, a periodic copolymer, a random copolymer, or a statistical copolymer.

In embodiments, monomers present in the polymer may, by way of non-limiting example, comprise one or more selected from the group consisting of acrylamide, 2-acrylamido-2-methylpropane sulfonic acid, acrylate, acrylic acid, acrylonitrile, acrylophenone, acryloyl chloride, actin nucleation core, adipic acid, adipoyl chloride, biphenyltetracarboxylic acid dianhydride, butadiene, 1,2,4-butanetriol, butene, butyl acrylate, butyl cyanoacrylate, butyl methacrylate, caprolactam, caprolactone, chloroprene, cyanoacrylate, cyclobutene, cycloheptene, cyclohexanedimethanol, cyclopentene, diamine, 2,4-diaminotoluene, 2,5-diaminotoluene, 2,3-dichlorobutadiene, dicyclopentadiene, dimer acid, 3,4-dimethoxystyrene, dimethyldiethoxysilane, diphenyl carbonate, dipropylene glycol, divinyl ether, divinylbenzene, ethyl acrylate, ethyl cyanoacrylate, ethyl methacrylate, ethylene, ethylene glycol dimethacrylate, ethylene oxide, ethylidene norbornene, furfural, glycidyl methacrylate, glycoluril, 1,5-hexadiene, 4,4'-(hexafluoroisopropylidene)dipthalic anhydride, hexamethylenediamine, 4-hydroxybenzoic acid, (hydroxyethyl)methacrylate, N-(2-hydroxypropyl) methacrylamide, ioxitalamic acid, isobutyl cyanoacrylate, isophthalic acid, isoprene, itaconic acid, lactic acid O-carboxyanhydride, lactide, methacrolein, methacrylamide, methacrylate, methacrylic acid, methacrylonitrile, methyl 2-chloroacrylate, methyl 2-fluoroacrylate, methyl acrylate, methyl cyanoacrylate, methyl isocyanate, methyl methacrylate, 4-methyl-1-pentene, N,N'-methylenebisacrylamide, methylene diphenyl diisocyanate, α-methylstyrene, neopentyl glycol, norbornene, 1,8-octanediol, octene, octyl cyanoacrylate, 2-octyl cyanoacrylate, p-phenylenediamine, propene, sebacoyl chloride, styrene, terephthalic acid, terephthaloyl chloride, tetrafluoroethylene, 2,2,4,4-tetramethyl-1,3-cyclobutanediol, tetramethylxylene diisocyanate, trimethylolpropane triacrylate, toluene diisocyanate, trimethylene carbonate, uvitic acid, uvitonic acid, vinyl acetate, vinyl chloride, vinyl ester, vinyl neodecanoate, vinyl propionate, N-vinylacetamide, 4-vinylbenzyl chloride, N-vinylcarbazole, vinylcyclohexene dioxide, 2-vinylpyridine, 4-vinylpyridine, N-vinylpyrrolidone, vinyl silane, vinylsulfonic acid, 4-vinyltoluene, and vinyltriethoxysilane. The polymer may comprise at least one monomer selected from the group consisting of acryloylmorpholine and N-isopropyl acrylamide.

In embodiments, the copolymer may comprise at least one monomer that is highly soluble, freely soluble, or soluble in the solvent and at least one monomer that is insoluble, poorly soluble, very slightly soluble, or slightly soluble in the solvent.

In embodiments, the chemical reaction may be selected from the group consisting of a transesterification reaction, an oxidation/reduction reaction, a group transfer reaction, a hydrolysis reaction, an isomerization reaction, and a dehydration reaction.

In embodiments, step d) may comprise changing a temperature of the solution to precipitate the enzyme-polymer conjugate.

In embodiments, step d) may comprise extracting the enzyme-polymer conjugate with an extractant. The enzyme-polymer conjugate may exhibit upper critical solution temperature (UCST) behavior in the solvent and lower critical solution temperature (LCST) behavior in the extractant. The enzyme-polymer conjugate may exhibit LCST behavior in the solvent and UCST behavior in the extractant.

It is another aspect of the present invention to provide a solution, comprising an organic solvent or ionic liquid; and an enzyme-polymer conjugate molecularly dissolved in the organic solvent or ionic liquid, wherein the enzyme-polymer conjugate is formed by reaction of an enzyme and a polymer, wherein a catalytic activity of the enzyme-polymer conjugate in the organic solvent or ionic liquid is greater than a catalytic activity of the enzyme alone in the organic solvent or ionic liquid.

In embodiments, the enzyme may be lipase.

In embodiments, the organic solvent or ionic liquid may be 1-butyl-3-methylimidazolium hexafluorophosphate.

In embodiments, the polymer may be a copolymer, and may, but need not, be a random copolymer. The copolymer may, but need not, comprise at least one monomer that is highly soluble, freely soluble, or soluble in the organic solvent or ionic liquid and at least one monomer that is insoluble, poorly soluble, very slightly soluble, or slightly soluble in the organic solvent or ionic liquid.

In embodiments, the polymer may comprise at least one monomer selected from the group consisting of acryloylmorpholine and N-isopropyl acrylamide.

It is another aspect of the present invention to provide an enzyme-polymer conjugate, wherein the polymer comprises a first monomer and a second monomer, wherein a ratio of the first monomer to the second monomer is selected to achieve a desired cloud point of the enzyme-polymer conjugate in a solvent.

In embodiments, the molar ratio of the first monomer to the second monomer may be between about 0.01:0.99 and about 0.99:0.01, or between about 0.58:0.42 and about 0.88:0.12.

In embodiments, the cloud point of the enzyme-polymer conjugate in the solvent may be between about 4° C. and about 78° C.

DETAILED DESCRIPTION OF THE INVENTION

Figure 1:
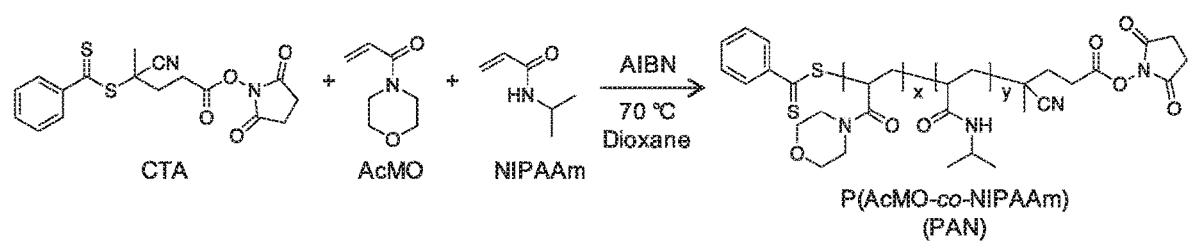
FIG. 1 is an illustration of a scheme for synthesizing N-hydroxysuccinimide ester (NHS)-terminated poly(acryloylmorpholine-ran-N-isopropyl acrylamide) (PAN) polymers by reversible addition-fragmentation chain-transfer polymerization (RAFT).

For purposes of further disclosure and to comply with applicable written description and enablement requirements, the following references generally relate to systems and methods for enzymatic biocatalysis, and are hereby incorporated by reference in their entireties:

Zhao, H. Methods for Stabilizing and Activating Enzymes in Ionic Liquids—A Review. J. Chem. Technol. Biotechnol. 2010, 85 (7), 891-907.

Pace, C. N.; Trevino, S.; Prabhakaran, E.; Scholtz, J. M. Protein Structure, Stability and Solubility in Water and Other Solvents. Philos. Trans. R. Soc. London Ser. B—Biological Sci. 2004, 359 (1448), 1225-1234.

Carrea, G.; Riva, S. Properties and Synthetic Applications of Enzymes in Organic Solvents. Angew. Chem. Int. Ed. Engl. 2000, 39 (13), 2226-2254.

Akbar, U.; Aschenbrenner, C. D.; Harper, M. R.; Johnson, H. R.; Dordick, J. S.; Clark, D. S. Direct Solubilization of Enzyme Aggregates with Enhanced Activity in Nonaqueous Media. Biotechnol. Bioeng. 2007, 96 (6), 1030-1039.

Panganiban, B.; Qiao, B.; Jiang, T.; DelRe, C.; Obadia, M. M.; Nguyen, T. D.; Smith, A. A. A.; Hall, A.; Sit, I.; Crosby, M. G.; et al. Random Heteropolymers Preserve Protein Function in Foreign Environments. Science (80-.). 2018, 359 (6381), 1239-1243.

Sheldon, R. A. Enzyme Immobilization: The Quest for Optimum Performance. Adv. Synth. Catal. 2007, 349 (8-9), 1289-1307.

Rodrigues, R. C.; Ortiz, C.; Berenguer-Murcia, Á.; Torres, R.; Fernández-Lafuente, R. Modifying Enzyme Activity and Selectivity by Immobilization. Chem. Soc. Rev. 2013, 42 (15), 6290-6307.

Hanefeld, U.; Gardossi, L.; Magner, E. Understanding Enzyme Immobilisation. Chem. Soc. Rev. 2009, 38 (2), 453-468.

Grazú, V.; López-Gallego, F.; Montes, T.; Abian, O.; González, R.; Hermoso, J. A.; García, J. L.; Mateo, C.; Guisán, J. M. Promotion of Multipoint Covalent Immobilization through Different Regions of Genetically Modified Penicillin G Acylase from E. Coli. Process Biochem. 2010, 45 (3), 390-398.

Tischer, W.; Kasche, V. Immobilized Enzymes: Crystals or Carriers? Trends Biotechnol. 1999, 17 (8), 326-335.

Liu, H.; Zhang, J.; Luo, X.; Kong, N.; Cui, L.; Liu, J. Preparation of Biodegradable and Thermoresponsive Enzyme-Polymer Conjugates with Controllable Bioactivity via RAFT Polymerization. Eur. Polym. J. 2013, 49 (10), 2949-2960.

Lou, L.-L.; Qu, H.; Yu, W.; Wang, B.; Ouyang, L.; Liu, S.; Zhou, W. Covalently Immobilized Lipase on a Thermoresponsive Polymer with an Upper Critical Solution Temperature as an Efficient and Recyclable Asymmetric Catalyst in Aqueous Media. Chem Cat Chem 2018, 10 (5), 1166-1172.

Limadinata, P. A.; Li, A.; Li, Z. Temperature-Responsive Nanobiocatalysts with an Upper Critical Solution Temperature for High Performance Biotransformation and Easy Catalyst Recycling: Efficient Hydrolysis of Cellulose to Glucose. Green Chem. 2015, 17 (2), 1194-1203.

Cummings, C.; Murata, H.; Koepsel, R.; Russell, A. J. Tailoring Enzyme Activity and Stability Using Polymer-Based Protein Engineering. Biomaterials 2013, 34 (30), 7437-7443.

Hoffman, A. S.; Stayton, P. S. Conjugates of Stimuli-Responsive Polymers and Proteins. Prog. Polym. Sci. 2007, 32 (8-9), 922-932.

Mackenzie, K. J.; Francis, M. B. Recyclable Thermoresponsive Polymer-Cellulase Bioconjugates for Biomass Depolymerization. J. Am. Chem. Soc. 2013, 135 (1), 293-300.

De, P.; Li, M.; Gondi, S. R.; Sumerlin, B. S. Temperature-Regulated Activity of Responsive Polymer-Protein Conjugates Prepared by Grafting—from via RAFT Polymerization. J. Am. Chem. Soc. 2008, 130 (34), 11288-11289.

Cobo, I.; Li, M.; Sumerlin, B. S.; Perrier, S. Smart Hybrid Materials by Conjugation of Responsive Polymers to Biomacromolecules. Nat. Mater. 2015, 14 (2), 143-149.

Zhang, Y.; Dai, Y.; Hou, M.; Li, T.; Ge, J.; Liu, Z. Chemo-Enzymatic Synthesis of Valrubicin Using Pluronic Conjugated Lipase with Temperature Responsiveness in Organic Media. RSC Adv. 2013, 3 (45), 22963-22966.

Zhu, J.; Zhang, Y.; Lu, D.; Zare, R. N.; Ge, J.; Liu, Z. Temperature-Responsive Enzyme-Polymer Nanoconjugates with Enhanced Catalytic Activities in Organic Media. Chem. Commun. 2013, 49 (54), 6090-6092.

Wu, X.; Ge, J.; Zhu, J.; Zhang, Y.; Yong, Y.; Liu, Z. A General Method for Synthesizing Enzyme-Polymer Conjugates in Reverse Emulsions Using Pluronic as a Reactive Surfactant. Chem. Commun. 2015, 51 (47), 9674-9677.

Behr, A.; Henze, G.; Schomäcker, R. Thermoregulated Liquid/Liquid Catalyst Separation and Recycling. Adv. Synth. Catal. 2006, 348 (12-13), 1485-1495.

Liu, C.; Jiang, J.; Wang, Y.; Cheng, F.; Jin, Z. Thermoregulated Phase Transfer Ligands and Catalysis XVIII: Synthesis of N,N-Dipolyoxyethylene-Substituted-2-(Diphenylphosphino)Phenylamine (PEO-DPPPA) and the Catalytic Activity of Its Rhodium Complex in the Aqueous-Organic Biphasic Hydroformylation of 1. J. Mol. Catal. A Chem. 2003, 198 (1-2), 23-27.

Jin, Z.; Zheng, X.; Fell, B. Thermoregulated Phase Transfer Ligands and Catalysis. I. Synthesis of Novel Polyether-Substituted Triphenylphosphines and Application of Their Rhodium Complexes in Two-Phase Hydroformylation. J. Mol. Catal. A Chem. 1997, 116 (1-2), 55-58.

Zheng, X.; Jiang, J.; Liu, X.; Jin, Z. Thermoregulated Phase Transfer Ligands and Catalysis. III. Aqueous/Organic Two-Phase Hydroformylation of Higher Olefins by Thermoregulated Phase-Transfer Catalysis. Catal. Today 1998, 44 (1-4), 175-182.

Chado, G. R.; Holland, E. N.; Tice, A. K.; Stoykovich, M. P.; Kaar, J. L. Modification of Lipase with Poly(4-Acryloylmorpholine) Enhances Solubility and Transesterification Activity in Anhydrous Ionic Liquids. Biomacromolecules 2018, 19 (4), 1324-1332.

Niskanen, J.; Tenhu, H. How to Manipulate the Upper Critical Solution Temperature (UCST)? Polym. Chem. 2017, 8 (1), 220-232.

Seuring, J.; Agarwal, S. Polymers with Upper Critical Solution Temperature in Aqueous Solution. Macromol. Rapid Commun. 2012, 33 (22), 1898-1920.

Seuring, J.; Agarwal, S. First Example of a Universal and Cost-Effective Approach: Polymers with Tunable Upper Critical Solution Temperature in Water and Electrolyte Solution. Macromolecules 2012, 45 (9), 3910-3918.

Asai, H.; Fujii, K.; Ueki, T.; Sawamura, S.; Nakamura, Y.; Kitazawa, Y.; Watanabe, M.; Han, Y. S.; Kim, T. H.; Shibayama, M. Structural Study on the UCST-Type Phase Separation of Poly(N-Isopropylacrylamide) in Ionic Liquid. Macromolecules 2013, 46 (3), 1101-1106.

Hunt, P. A.; Ashworth, C. R.; Matthews, R. P. Hydrogen Bonding in Ionic Liquids. Chem. Soc. Rev. 2015, 44 (5), 1257-1288.

Cummings, C. S.; Murata, H.; Matyjaszewski, K.; Russell, A. J. Polymer-Based Protein Engineering Enables Molecular Dissolution of Chymotrypsin in Acetonitrile. ACS Macro Lett. 2016, 5, 493-497.

Ueki, T. Stimuli-Responsive Polymers in Ionic Liquids. Polym. J. 2014, 46 (10), 646-655.

Depp, V.; Kaar, J. L.; Russell, A. J.; Lele, B. S. Enzyme Sheathing Enables Nanoscale Solubilization of Biocatalyst and Dramatically Increases Activity in Organic Solvent. Biomacromolecules 2008, 9 (4), 1348-1351.

Brogan, A. P. S.; Hallett, J. P. Solubilizing and Stabilizing Proteins in Anhydrous Ionic Liquids through Formation of Protein-Polymer Surfactant Nanoconstructs. J. Am. Chem. Soc. 2016, 138 (13), 4494-4501.

Brogan, A. P. S.; Bui-Le, L.; Hallett, J. P. Non-Aqueous Homogenous Biocatalytic Conversion of Polysaccharides in Ionic Liquids Using Chemically Modified Glucosidase. Nat. Chem. 2018, 10 (8), 859-865.

Panza, J. L.; Russell, A. J.; Beckman, E. J. Fluorinated NAD as an Affinity Surfactant. Chem. Commun. 2002, 0 (9), 928-929.

Dong, X. H.; Obermeyer, A. C.; Olsen, B. D. Three-Dimensional Ordered Antibody Arrays Through Self-Assembly of Antibody-Polymer Conjugates. Angew. Chemie—Int. Ed. 2017, 56 (5), 1273-1277.

Lam, C. N.; Kim, M.; Thomas, C. S.; Chang, D.; Sanoja, G. E.; Okwara, C. U.; Olsen, B. D. The Nature of Protein Interactions Governing Globular Protein-Polymer Block Copolymer Self-Assembly. Biomacromolecules 2014, 15 (4), 1248-1258.

Obermeyer, A. C.; Olsen, B. D. Synthesis and Application of Protein-Containing Block Copolymers. ACS Macro Lett. 2015, 101-110.

Shimoboji, T.; Ding, Z. L.; Stayton, P. S.; Hoffman, A. S. Photoswitching of Ligand Association with a Photoresponsive Polymer-Protein Conjugate. Bioconjug. Chem. 2002, 13 (5), 915-919.

Ueki, T.; Nakamura, Y.; Yamaguchi, A.; Niitsuma, K.; Lodge, T. P.; Watanabe, M. UCST Phase Transition of Azobenzene-Containing Random Copolymer in an Ionic Liquid. Macromolecules 2011, 44 (17), 6908-6914.

Shimoboji, T.; Larenas, E.; Fowler, T.; Kulkarni, S.; Hoffman, A. S.; Stayton, P. S. Photoresponsive Polymer-Enzyme Switches. Proc. Natl. Acad. Sci. U.S.A 2002, 99 (26), 16592-16596.

Murata, H.; Cummings, C. S.; Koepsel, R. R.; Russell, A. J. Polymer-Based Protein Engineering Can Rationally Tune Enzyme Activity, PH-Dependence, and Stability. Biomacromolecules 2013, 14 (6), 1919-1926.

Bulmus, V.; Ding, Z.; Long, C. J.; Stayton, P. S.; Hoffman, A. S. Site-Specific Polymer-Streptavidin Bioconjugate for PH-Controlled Binding and Triggered Release of Biotin. Bioconjug. Chem. 2000, 11 (1), 78-83.

Chen, L.; Honma, Y.; Mizutani, T.; Liaw, D.-J.; Gong, J.; Osada, Y. Effects of Polyelectrolyte Complexation on the UCST of Zwitterionic Polymer. Polymer (Guildf). 2000, 41 (1), 141-147.

Cassano, R.; Mellace, S.; Trombino, S. Responsive Polymer-Biomacromolecule Conjugates for Drug Delivery. Stimuli Responsive Polym. Nanocarriers Drug Deliv. Appl. Vol. 1 2018, 433-452.

U.S. Patent Application Publication 2018/0051271, entitled "Non-aqueous enzyme-polymer conjugate solutions and related methods," published 22 Feb. 2018 to Russell et al. ("Russell").

The present invention provides novel methods and systems for rationally tuning the interactions of an enzyme (e.g. lipase ("LipA")) and a solvent (e.g. 1-butyl-3-methylimidazolium hexafluorophosphate ("[BMIM][PF$_6$]") in a thermoresponsive manner within a desired temperature range. This tuning is accomplished by modifying the enzyme with a polymer, e.g. an acryloylmorpholine ("AcMO")-co-N-isopropyl acrylamide ("NIPAAm") polymer, which imparts an upper critical solution temperature ("UCST")-type phase behavior and/or a lower critical solution temperature ("LCST")-type phase behavior to the enzyme-polymer conjugate in the desired temperature range. By altering the composition of the polymer, particularly the ratio of monomer units in a copolymer (e.g. a poly(acryloylmorpholine-co-N-isopropyl acrylamide) ("PAN") copolymer), the cloud point of the resulting enzyme-polymer conjugate in the solvent can be reliably controlled.

Unexpectedly, the interactions of an enzyme and a solvent may be tuned in a thermoresponsive manner by modifying the enzyme with a polymer to impart UCST- and/or LCST-type phase behavior to the enzyme-polymer conjugate within a desired temperature range. Generally, the polymer, e.g. one or more monomers, and the relative molar amounts thereof in the polymer, may be selected based on the enzyme to be modified and the solvent in which the enzyme-catalyzed reaction will be carried out. In some embodiments, the polymer can be a homopolymer where the homopolymer-enzyme conjugate is miscible in the solvent at an operational temperature, but immiscible either above or below the operating temperature, which allows the enzyme of the homopolymer-enzyme conjugate to be recycled. Where the polymer is a copolymer, the monomers may be selected such that one or more monomers of the copolymer is highly soluble, freely soluble, or soluble in the preselected solvent and one or more other monomers is poorly soluble or insoluble, slightly soluble, or very slightly soluble in the preselected solvent. The terms highly soluble, poorly soluble, insoluble, etc. are to be understood as set forth below:

| Term | Mass parts of solvent required to dissolve 1 mass part of solute |
|---|---|
| Highly soluble | <1 |
| Freely soluble | 1 to 10 |
| Soluble | 10 to 30 |
| Sparingly soluble | 30 to 100 |
| Slightly soluble | 100 to 1000 |
| Very slightly soluble | 1000 to 10,000 |
| Poorly insoluble or insoluble | ≥10,000 |

The solubility of a monomer in the preselected solvent may be estimated, in the first instance, by any suitable metric or method familiar to those skilled in the art, including but not limited to Hildebrand solubility parameters and Hansen solubility parameters. As a first non-limiting example, where the desired or preselected solvent has a relatively low Hildebrand solubility parameter, e.g. n-pentane, the monomers of the polymer may comprise one or more monomers that form polymers having relatively low Hildebrand solubility parameters (and are thus likely to be highly soluble in the solvent), e.g. tetrafluoroethylene or ethylene, and one or more monomers that form polymers having relatively high Hildebrand solubility parameters (and are thus likely to be poorly soluble or insoluble in the solvent), e.g. ethylene glycol or (hydroxyethyl)methacrylate. As a second non-limiting example, where the desired or preselected solvent has a relatively high Hildebrand solubility parameter, e.g. ethanol, the monomers of the polymer may comprise one or more monomers that form polymers having relatively high Hildebrand solubility parameters (and are thus likely to be highly soluble in the solvent), e.g. ethylene glycol or (hydroxyethyl)methacrylate, and one or more monomers that form polymers having relatively low Hildebrand solubility parameters (and are thus likely to be poorly soluble or insoluble in the solvent), e.g. tetrafluoroethylene or ethylene. As a third non-limiting example, where the desired or preselected solvent has an intermediate Hildebrand solubility parameter, e.g. chloroform, the monomers of the polymer may comprise one or more monomers that form polymers having intermediate Hildebrand solubility parameters (and are thus likely to be highly soluble in the solvent), e.g. phenylene oxide or methyl methacrylate, and one or more monomers that form polymers having relatively low or high Hildebrand solubility parameters (and are thus likely to be poorly soluble or insoluble in the solvent), e.g. tetrafluoroethylene or ethylene glycol.

After selection of the monomer(s) for the polymer based on the desired or preselected combination of enzyme and solvent, the thermodynamic favorability of interactions between the polymer and the solvent may be made highly sensitive to temperature by varying the relative molar amounts of each monomer in the polymer. The composition of the polymer will also depend on whether the polymer is likely to exhibit UCST-type behavior (i.e. the polymer is soluble at temperatures above the cloud point and insoluble at temperatures below the cloud point) or LCST-type behavior (i.e. the polymer is soluble at temperatures below the cloud point and insoluble at temperatures above the cloud point) in the desired or preselected solvent. Because the cloud point is dependent on the composition of the polymer, varying the relative amounts of monomer provides a simple method for tuning the cloud point of the polymer in the solvent. As such, the total thermodynamic favorability of the interactions between the enzyme-polymer conjugates and the solvent are also highly temperature-dependent; specifically, the present inventors have found that modification of enzymes with appropriate polymers facilitates dissolution of the enzyme above the cloud point of the conjugate and separation of the enzyme below the cloud point (i.e. UCST-type behavior), or vice versa (i.e. LCST-type behavior).

An aspect of the invention is a copolymer-enzyme, wherein the copolymer of the copolymer-enzyme comprises a first monomer and a second monomer. The first monomer is highly soluble, soluble, or freely soluble in a reaction solvent. The second monomer is insoluble, slightly soluble, or very slightly soluble in the solvent. The enzyme and solvent can be selected based on the end use (i.e. the reaction) utilizing the system.

The first monomer is present in the copolymer in an amount between about 1 vol. % and about 99 vol. %. The second monomer is present in the copolymer in an amount between about 1 vol. % and about 99 vol. %, or the balance of the system. Incidental materials can be present in the copolymer in an amount not to exceed about 99 vol. %. The copolymer can be present in the system in an amount of between about 1 vol. % and about 99 vol. %. The enzyme can be present in the system in an amount between about 1 vol. % and about 99 vol. %. The solvent can be present in an amount between about 1 vol. % and about 99 vol. %; in some embodiments, the balance can be the solvent. Incidental materials can be present in the system in an amount not to exceed about 99 vol. % of the system. It is to be expressly understood that the values described in this paragraph may take any value that is about any whole number within the described range.

The molecular weight of the enzyme-polymer conjugate can be any suitable molecular weight and fall within any suitable range of molecular weights. By way of non-limiting example, the molecular weight of the enzyme-polymer conjugate may be at least about 1 kDa, at least about 10 kDa, at least about 20 kDa, at least about 30 kDa, at least about 40 kDa, at least about 50 kDa, at least about 60 kDa, at least about 70 kDa, at least about 80 kDa, at least about 90 kDa, at least about 100 kDa, at least about 110 kDa, at least about 120 kDa, at least about 130 kDa, at least about 140 kDa, at least about 150 kDa, at least about 160 kDa, at least about 170 kDa, at least about 180 kDa, at least about 190 kDa, at least about 200 kDa, at least about 210 kDa, at least about 220 kDa, at least about 230 kDa, at least about 240 kDa, at least about 250 kDa, at least about 260 kDa, at least about 270 kDa, at least about 280 kDa, at least about 290 kDa, at least about 300 kDa, at least about 310 kDa, at least about 320 kDa, at least about 330 kDa, at least about 340 kDa, or at least about 350 kDa. Additionally or alternatively, by way of further non-limiting example, the molecular weight of the enzyme-polymer conjugate may be no more than about 360 kDa, no more than about 350 kDa, no more than about 340 kDa, no more than about 330 kDa, no more than about 320 kDa, no more than about 310 kDa, no more than about 300 kDa, no more than about 290 kDa, no more than about 280 kDa, no more than about 270 kDa, no more than about 260 kDa, no more than about 250 kDa, no more than about 240 kDa, no more than about 230 kDa, no more than about 220 kDa, no more than about 210 kDa, no more than about 200 kDa, no more than about 190 kDa, no more than about 180 kDa, no more than about 170 kDa, no more than about 160 kDa, no more than about 150 kDa, no more than about 140 kDa, no more than about 130 kDa, no more than about 120 kDa, no more than about 110 kDa, no more than about 100 kDa, no more than about 90 kDa, no more than about 80 kDa, no more than about 70 kDa, no more than about 60 kDa, no more than about 50 kDa, no more than about 40 kDa, no more than about 30 kDa, no more than about 20 kDa, or no more than about 10 kDa. Additionally or alternatively, by way of further non-limiting example, the molecular weight of the enzyme-polymer conjugate can be about any whole number of kilodaltons between about 1 kDa and about 360 kDa.

Enzyme-polymer conjugates of the present invention may be further characterized as having other properties, such a desired or preselected site of attachment of the polymer to the enzyme, a desired or preselected hydrodynamic radius (e.g. about any number of hundredths of a nanometer between about 0.01 nm and about 50 nm), and/or a desired or preselected zeta potential (e.g. about any number of tenths of millivolts between about −75 mV and 75 mV).

Although efforts have been made to include several potential solvents and enzymes in the present disclosure, one skilled in the art would understand that other enzymes and solvents can be used with this invention, without deviating from the invention.

The enzyme may, by way of non-limiting example, comprise an oxidoreductase, e.g. an alcohol oxidoreductase, an aldehyde/oxo oxidoreductase, a CH—CH oxidoreductase, a CH—NH$_2$ oxidoreductase (such as an amino acid oxidoreductase), a CH—NH oxidoreductase, an NADH or NADPH oxidoreductase, a nitrogenous donor oxidoreductase, a sulfur oxidoreductase, a diphenol family oxidoreductase, a peroxidase, a monooxygenase, or a dioxygenase (such as a steroid hydroxylase); a transferase, e.g. a one carbon transferase, an aldehyde-ketone transferase, an acyltransferase, a glycosyltransferase, an alkyl or aryl transferase, a nitrogenous transferase, a phosphorous-containing transferase, a sulfur-containing transferase, or a selenium-containing transferase; a hydrolase, e.g. an esterase, a sugar hydrolase, an ether bond hydrolase, a protease, a carbon-nitrogen non-peptide hydrolase, an acid anhydride hydrolase, or a carbon-carbon hydrolase; a lyase, e.g. a carbon-carbon lyase, a carbon-oxygen lyase (such as a dehydratase), a carbon-nitrogen lyase, a carbon-sulfur lyase, a carbon-halide lyase, or a phosphorus-oxygen lyase; an isomerase, e.g. an epimerase or racemase, a geometric isomerase, an intramolecular oxidoreductase, a mutase, an intramolecular lyase, or a topoisomerase; a ligase, e.g. a carbon-oxygen ligase, a carbon-sulfur ligase, a carbon-nitrogen ligase, a carbon-carbon ligase, or a phosphoric ester or nitrogen-metal ligase; or a translocase. In embodiments, the enzyme may be lipase.

The enzyme-polymer can be provided in a solvent, which is the same solvent used in the reaction that the enzyme is supporting. The solvent may, by way of non-limiting example, comprise an alcohol, e.g. tert-amyl alcohol, benzyl alcohol, 1,4-butanediol, 1,2,4-butanetriol, butanol (such as 2-butanol, N-butanol, or tert-butanol), di(propylene glycol) methyl ether, diethylene glycol, ethanol, ethylene glycol, 2-ethylhexanol, furfuryl alcohol, glycerol, isobutanol, isopropyl alcohol, methanol, 2-(2-methoxyethoxy)ethanol, 2-methyl-1-butanol, 2-methyl-1-pentanol, 3-methyl-2-butanol, neopentyl alcohol, 2-pentanol, 1,3-propanediol, 1-propanol, propylene glycol, or propylene glycol methyl ether; an amide, e.g. dimethylacetamide, dimethylformamide, formamide, N-formylmorpholine, N-methyl-2-pyrrolidone, N-methylformamide, 2-pyrrolidone, tetramethylurea, N-vinylacetamide, or N-vinylpyrrolidone; an amine, e.g. collidine, diethylenetriamine, ethylenediamine, morpholine, piperidine, pyridine, pyrrolidine, quinoline, tetrahydroquinoline, or tributylamine; an aromatic solvent, e.g. benzene, benzonitrile, benzyl alcohol, chlorobenzene, dibenzyl ether, 1,2-dichlorobenzene, 1,2-difluorobenzene, hexafluorobenzene, mesitylene, nitrobenzene, pyridine, tetralin, toluene, 1,2,4-trichlorobenzene, trifluorotoluene, or xylene; an ester, e.g. benzyl benzoate, bis(2-ethylhexyl) adipate, bis(2-ethylhexyl) phthalate, 2-butoxyethanol acetate, butyl acetate (such as sec-butyl acetate or tert-butyl acetate), diethyl carbonate, dimethyl adipate, dioctyl terephthalate, ethyl acetate, ethyl acetoacetate, ethyl butyrate, ethyl lactate, ethylene carbonate, hexyl acetate, isoamyl acetate, isobutyl acetate, isopropyl acetate, methyl acetate, methyl lactate, methyl phenylacetate, methyl propionate, propyl acetate, propylene carbonate, or triacetin; an ether, e.g. tert-amyl ethyl ether, cyclopentyl methyl ether, di-tert-butyl ether, di(propylene glycol) methyl ether, dibutyl ether, diethyl ether, diisopropyl ether, dimethoxyethane, dimethoxymethane, 1,4-dioxane, ethyl tert-butyl ether, methoxyethane, 2-(2-methoxyethoxy)ethanol, methyl tert-butyl ether, 2-methyltetrahydrofuran, morpholine, polyethylene glycol, propylene glycol methyl ether, tetrahydrofuran, tetrahydrofuryl alcohol, tetrahydropyran, or 2,2,5,5-tetramethyltetrahydrofuran; a halogenated solvent, e.g. benzotrichloride, bromoform, bromomethane, carbon tetrachloride, 2-chloro-1,1,1-trifluoroethane, chlorobenzene, chloroform, chloromethane, 1,1-dichloro-1-fluoroethane, 1,2-dichlorobenzene, 1,1-dichloroethane, 1,2-dichloroethane, 1,1-dichloroethene, 1,2-dichloroethene, dichloromethane, 1,2-difluorobenzene, 1,2-diiodoethylene, diiodomethane, FC-75, hexachlorobutadiene, hexafluoro-2-propanol, parachlorobenzotrifluoride, perfluoro-1,3-dimethylcyclohexane, perfluorocyclohexane, perfluorodecalin, perfluorohexane, perfluoromethylcyclohexane, perfluoromethyldecalin, perfluorooctane, perfluorotoluene, perfluorotripentylamine, tetrabromomethane, 1,1,1,2-tetrachloroethane, 1,1,2,2-tetrachloroethane, tetrachloroethylene, 1,2,4-trichlorobenzene, 1,1,1-trichloroethane, 1,1,2-trichloroethane, trichloroethylene, 1,2,3-trichloropropane, 2,2,2-trifluoroethanol, or trifluorotoluene; a hydrocarbon, e.g. benzene, cycloheptane, cyclohexane, cyclohexene, cyclooxtane, cyclopentane, decalin, diesel fuel, dodecane, durene, heptane, hexane, kerosene, ligroin, limonene, mesitylene, methylcyclohexane, naphtha, Nujol, octadecene, pentamethylbenzene, pentane, petroleum benzine, petroleum ether, toluene, tridecane, turpentine, white spirit, or xylene; an inorganic solvent, e.g. ammonia, carbon dioxide, carbon disulfide, carbon tetrachloride, hydrogen fluoride, a molten salt, phosphorus tribromide, sulfur dioxide, sulfuric acid, sulfuryl chloride fluoride, or water; an ionic liquid, e.g. Aliquat 336, 1-butyl-3-methylimidazolium hexafluorophosphate, 1-butyl-3-methylimidazolium tetrachloroferrate, a deep eutectic solvent, 1-ethyl-3-methylimidazolium chloride, ethylammonium nitrate, fluoroantimonic acid, methylpridinium, a molten salt, or trioctylmethylammonium bis(trifluoromethylsulfonyl)imide; a ketone, e.g. acetone, acetophenone, butanone, cyclopentanone, ethyl isopropyl ketone, 2-hexanone, isophorone, β-isophorone, mesityl oxide, methyl isobutyl ketone, methyl isopropyl ketone, 3-methyl-2-pentanone, 2-pentanone, or 3-pentanone; or a nitro solvent, e.g. nitrobenzene, nitroethane, nitromethane, 1-nitropropane, or 2-nitropropane. In embodiments, the solvent may be 1-butyl-3-methylimidazolium hexafluorophosphate.

In embodiments, the polymer may be a copolymer. The polymer may be an alternating copolymer, a block copolymer, a gradient copolymer, a periodic copolymer, a random copolymer, or a statistical copolymer.

Monomers present in the polymer may, by way of non-limiting example, comprise one or more selected from the group consisting of acrylamide, 2-acrylamido-2-methylpropane sulfonic acid, acrylate, acrylic acid, acrylonitrile, acrylophenone, acryloyl chloride, actin nucleation core, adipic acid, adipoyl chloride, biphenyl-tetracarboxylic acid dianhydride, butadiene, 1,2,4-butanetriol, butene, butyl acrylate, butyl cyanoacrylate, butyl methacrylate, caprolactam, caprolactone, chloroprene, cyanoacrylate, cyclobutene, cycloheptene, cyclohexanedimethanol, cyclopentene, diamine, 2,4-diaminotoluene, 2,5-diaminotoluene, 2,3-dichlorobutadiene, dicyclopentadiene, dimer acid, 3,4-dimethoxystyrene, dimethyldiethoxysilane, diphenyl carbonate, dipropylene glycol, divinyl ether, divinylbenzene, ethyl acrylate, ethyl cyanoacrylate, ethyl methacrylate, ethylene, ethylene glycol dimethacrylate, ethylene oxide, ethylidene norbornene, furfural, glycidyl methacrylate, glycoluril, 1,5-hexadiene, 4,4'-(hexafluoroisopropylidene)dipthalic anhydride, hexamethylenediamine, 4-hydroxybenzoic acid, (hydroxyethyl)methacrylate, N-(2-hydroxypropyl) methacrylamide, ioxitalamic acid, isobutyl cyanoacrylate, isophthalic acid, isoprene, itaconic acid, lactic acid O-carboxyanhydride, lactide, methacrolein, methacrylamide, methacrylate, methacrylic acid, methacrylonitrile, methyl 2-chloroacrylate, methyl 2-fluoroacrylate, methyl acrylate, methyl cyanoacrylate, methyl isocyanate, methyl methacrylate, 4-methyl-1-pentene, N,N'-methylenebisacrylamide, methylene diphenyl diisocyanate, α-methylstyrene, neopentyl glycol, norbornene, 1,8-octanediol, octene, octyl cyanoacrylate, 2-octyl cyanoacrylate, p-phenylenediamine, propene, sebacoyl chloride, styrene, terephthalic acid, terephthaloyl chloride, tetrafluoroethylene, 2,2,4,4-tetramethyl-1,3-cyclobutanediol, tetramethylxylene diisocyanate, trimethylolpropane triacrylate, toluene diisocyanate, trimethylene carbonate, uvitic acid, uvitonic acid, vinyl acetate, vinyl chloride, vinyl ester, vinyl neodecanoate, vinyl propionate, N-vinylacetamide, 4-vinylbenzyl chloride, N-vinylcarbazole, vinylcyclohexene dioxide, 2-vinylpyridine, 4-vinylpyridine, N-vinylpyrrolidone, vinyl silane, vinylsulfonic acid, 4-vinyltoluene, and vinyltriethoxysilane. The polymer may comprise at least one monomer selected from the group consisting of acryloylmorpholine and N-isopropyl acrylamide.

An aspect of the invention is a method of forming the polymer-enzyme solvent system. The method includes combining a copolymer, wherein the copolymer comprises a first monomer and a second monomer. The first monomer is highly soluble, soluble, or freely soluble in the solvent. The second monomer is insoluble, slightly soluble, or very slightly soluble in the solvent. The enzyme and solvent can be selected based on the end use (i.e. the reaction) utilizing the system. Between about 1 vol. % and about 99 vol. % of the first polymer is combined with the second monomer in an amount between about 1 vol. % and about 99 vol. %, or the balance of the system. Incidental materials can be present in the copolymer in an amount not to exceed about 99 vol. %. The copolymer can be formed in a buffer solution at a pH between about 0 and about 14, in some embodiments about 7.9. The pH can be adjusted as required with an acid or base as would be known to one skilled in the art. The copolymer can be mixed at a temperature between about 0° C. and about 100° C., in some embodiments about 25° C., for between about one minute and about 24 hours.

The polymer in an amount of between about 1 vol. % and about 99 vol. % can be combined with one or more enzymes, where the total amount of the enzyme in the system is between about 1 vol. % and about 99 vol. %. Excess enzyme can be removed by passing the enzyme-polymer conjugate over a suitable cartridge (for example a nickel cartridge) to remove the excess enzyme. The solvent can be mixed with the polymer and enzyme in an amount between about 1 vol. % and about 99 vol. %; in some embodiments, the balance can be the solvent. Incidental materials can be present in the system in an amount not to exceed about 99 vol. % of the system.

The solution of the enzyme-polymer conjugate in the solvent may, but need not, further comprise one or more additives. As a first non-limiting example, the solution may comprise a salt that contains counterions that bind to the enzyme and increase its hydration, e.g. to improve the activity of the enzyme. As a second non-limiting example, the solution may comprise a salt hydrate, e.g. to control the amount of water that is available to the enzyme, which can impact the activity of the enzyme. As a third non-limiting example, the solution may comprise a co-solvent, e.g. to increase the solubility of a reaction substrate and/or product.

The enzyme may, by way of non-limiting example, comprise an oxidoreductase, e.g. an alcohol oxidoreductase, an aldehyde/oxo oxidoreductase, a CH—CH oxidoreductase, a CH—NH$_2$ oxidoreductase (such as an amino acid oxidoreductase), a CH—NH oxidoreductase, an NADH or NADPH oxidoreductase, a nitrogenous donor oxidoreductase, a sulfur oxidoreductase, a diphenol family oxidoreductase, a peroxidase, a monooxygenase, or a dioxygenase (such as a steroid hydroxylase); a transferase, e.g. a one carbon transferase, an aldehyde-ketone transferase, an acyltransferase, a glycosyltransferase, an alkyl or aryl transferase, a nitrogenous transferase, a phosphorous-containing transferase, a sulfur-containing transferase, or a selenium-containing transferase; a hydrolase, e.g. an esterase, a sugar hydrolase, an ether bond hydrolase, a protease, a carbon-nitrogen non-peptide hydrolase, an acid anhydride hydrolase, or a carbon-carbon hydrolase; a lyase, e.g. a carbon-carbon lyase, a carbon-oxygen lyase (such as a dehydratase), a carbon-nitrogen lyase, a carbon-sulfur lyase, a carbon-halide lyase, or a phosphorus-oxygen lyase; an isomerase, e.g. an epimerase or racemase, a geometric isomerase, an intramolecular oxidoreductase, a mutase, an intramolecular lyase, or a topoisomerase; a ligase, e.g. a carbon-oxygen ligase, a carbon-sulfur ligase, a carbon-nitrogen ligase, a carbon-carbon ligase, or a phosphoric ester or nitrogen-metal ligase; or a translocase. In embodiments, the enzyme may be lipase.

The enzyme-polymer can be provided in a solvent, which is the same solvent used in the reaction that the enzyme is supporting. The solvent may, by way of non-limiting example, comprise an alcohol, e.g. tert-amyl alcohol, benzyl alcohol, 1,4-butanediol, 1,2,4-butanetriol, butanol (such as 2-butanol, N-butanol, or tert-butanol), di(propylene glycol) methyl ether, diethylene glycol, ethanol, ethylene glycol, 2-ethylhexanol, furfuryl alcohol, glycerol, isobutanol, isopropyl alcohol, methanol, 2-(2-methoxyethoxy)ethanol, 2-methyl-1-butanol, 2-methyl-1-pentanol, 3-methyl-2-butanol, neopentyl alcohol, 2-pentanol, 1,3-propanediol, 1-propanol, propylene glycol, or propylene glycol methyl ether; an amide, e.g. dimethylacetamide, dimethylformamide, formamide, N-formylmorpholine, N-methyl-2-pyrrolidone, N-methylformamide, 2-pyrrolidone, tetramethylurea, N-vinylacetamide, or N-vinylpyrrolidone; an amine, e.g. collidine, diethylenetriamine, ethylenediamine, morpholine, piperidine, pyridine, pyrrolidine, quinoline, tetrahydroquinoline, or tributylamine; an aromatic solvent, e.g. benzene, benzonitrile, benzyl alcohol, chlorobenzene, dibenzyl ether, 1,2-dichlorobenzene, 1,2-difluorobenzene, hexafluorobenzene, mesitylene, nitrobenzene, pyridine, tetralin, toluene, 1,2,4-trichlorobenzene, trifluorotoluene, or xylene; an ester, e.g. benzyl benzoate, bis(2-ethylhexyl) adipate, bis(2-ethylhexyl) phthalate, 2-butoxyethanol acetate, butyl acetate (such as sec-butyl acetate or tert-butyl acetate), diethyl carbonate, dimethyl adipate, dioctyl terephthalate, ethyl acetate, ethyl acetoacetate, ethyl butyrate, ethyl lactate, ethylene carbonate, hexyl acetate, isoamyl acetate, isobutyl acetate, isopropyl acetate, methyl acetate, methyl lactate, methyl phenylacetate, methyl propionate, propyl acetate, propylene carbonate, or triacetin; an ether, e.g. tert-amyl ethyl ether, cyclopentyl methyl ether, di-tert-butyl ether, di(propylene glycol) methyl ether, dibutyl ether, diethyl ether, diisopropyl ether, dimethoxyethane, dimethoxymethane, 1,4-dioxane, ethyl tert-butyl ether, methoxyethane, 2-(2-methoxyethoxy)ethanol, methyl tert-butyl ether, 2-methyltetrahydrofuran, morpholine, polyethylene glycol, propylene glycol methyl ether, tetrahydrofuran, tetrahydrofuryl alcohol, tetrahydropyran, or 2,2,5,5-tetramethyltetrahydrofuran; a halogenated solvent, e.g. benzotrichloride, bromoform, bromomethane, carbon tetrachloride, 2-chloro-1,1,1-trifluoroethane, chlorobenzene, chloroform, chloromethane, 1,1-dichloro-1-fluoroethane, 1,2-dichlorobenzene, 1,1-dichloroethane, 1,2-dichloroethane, 1,1-dichloroethene, 1,2-dichloroethene, dichloromethane, 1,2-difluorobenzene, 1,2-diiodoethylene, diiodomethane, FC-75, hexachlorobutadiene, hexafluoro-2-propanol, parachlorobenzotrifluoride, perfluoro-1,3-dimethylcyclohexane, perfluorocyclohexane, perfluorodecalin, perfluorohexane, perfluoromethylcyclohexane, perfluoromethyldecalin, perfluorooctane, perfluorotoluene, perfluorotripentylamine, tetrabromomethane, 1,1,1,2-tetrachloroethane, 1,1,2,2-tetrachloroethane, tetrachloroethylene, 1,2,4-trichlorobenzene, 1,1,1-trichloroethane, 1,1,2-trichloroethane, trichloroethylene, 1,2,3-trichloropropane, 2,2,2-trifluoroethanol, or trifluorotoluene; a hydrocarbon, e.g. benzene, cycloheptane, cyclohexane, cyclohexene, cyclooxtane, cyclopentane, decalin, diesel fuel, dodecane, durene, heptane, hexane, kerosene, ligroin, limonene, mesitylene, methylcyclohexane, naphtha, Nujol, octadecene, pentamethylbenzene, pentane, petroleum benzine, petroleum ether, toluene, tridecane, turpentine, white spirit, or xylene; an inorganic solvent, e.g. ammonia, carbon dioxide, carbon disulfide, carbon tetrachloride, hydrogen fluoride, a molten salt, phosphorus tribromide, sulfur dioxide, sulfuric acid, sulfuryl chloride fluoride, or water; an ionic liquid, e.g. Aliquat 336, 1-butyl-3-methylimidazolium hexafluorophosphate, 1-butyl-3-methylimidazolium tetrachloroferrate, a deep eutectic solvent, 1-ethyl-3-methylimidazolium chloride, ethylammonium nitrate, fluoroantimonic acid, methylpridinium, a molten salt, or trioctylmethylammonium bis(trifluoromethylsulfonyl)imide; a ketone, e.g. acetone, acetophenone, butanone, cyclopentanone, ethyl isopropyl ketone, 2-hexanone, isophorone, β-isophorone, mesityl oxide, methyl isobutyl ketone, methyl isopropyl ketone, 3-methyl-2-pentanone, 2-pentanone, or 3-pentanone; or a nitro solvent, e.g. nitrobenzene, nitroethane, nitromethane, 1-nitropropane, or 2-nitropropane. In embodiments, the solvent may be 1-butyl-3-methylimidazolium hexafluorophosphate.

In embodiments, the polymer may be a copolymer. The polymer may be an alternating copolymer, a block copolymer, a gradient copolymer, a periodic copolymer, a random copolymer, or a statistical copolymer.

Monomers present in the polymer may, by way of non-limiting example, comprise one or more selected from the group consisting of acrylamide, 2-acrylamido-2-methylpropane sulfonic acid, acrylate, acrylic acid, acrylonitrile, acrylophenone, acryloyl chloride, actin nucleation core, adipic acid, adipoyl chloride, biphenyl-tetracarboxylic acid dianhydride, butadiene, 1,2,4-butanetriol, butene, butyl acrylate, butyl cyanoacrylate, butyl methacrylate, caprolactam, caprolactone, chloroprene, cyanoacrylate, cyclobutene, cycloheptene, cyclohexanedimethanol, cyclopentene, diamine, 2,4-diaminotoluene, 2,5-diaminotoluene, 2,3-dichlorobutadiene, dicyclopentadiene, dimer acid, 3,4-dimethoxystyrene, dimethyldiethoxysilane, diphenyl carbonate, dipropylene glycol, divinyl ether, divinylbenzene, ethyl acrylate, ethyl cyanoacrylate, ethyl methacrylate, ethylene, ethylene glycol dimethacrylate, ethylene oxide, ethylidene norbornene, furfural, glycidyl methacrylate, glycoluril, 1,5-hexadiene, 4,4'-(hexafluoroisopropylidene)dipthalic anhydride, hexamethylenediamine, 4-hydroxybenzoic acid, (hydroxyethyl)methacrylate, N-(2-hydroxypropyl) methacrylamide, ioxitalamic acid, isobutyl cyanoacrylate, isophthalic acid, isoprene, itaconic acid, lactic acid O-carboxyanhydride, lactide, methacrolein, methacrylamide, methacrylate, methacrylic acid, methacrylonitrile, methyl 2-chloroacrylate, methyl 2-fluoroacrylate, methyl acrylate, methyl cyanoacrylate, methyl isocyanate, methyl methacrylate, 4-methyl-1-pentene, N,N'-methylenebisacrylamide, methylene diphenyl diisocyanate, α-methylstyrene, neopentyl glycol, norbornene, 1,8-octanediol, octene, octyl cyanoacrylate, 2-octyl cyanoacrylate, p-phenylenediamine, propene, sebacoyl chloride, styrene, terephthalic acid, terephthaloyl chloride, tetrafluoroethylene, 2,2,4,4-tetramethyl-1,3-cyclobutanediol, tetramethylxylene diisocyanate, trimethylolpropane triacrylate, toluene diisocyanate, trimethylene carbonate, uvitic acid, uvitonic acid, vinyl acetate, vinyl chloride, vinyl ester, vinyl neodecanoate, vinyl propionate, N-vinylacetamide, 4-vinylbenzyl chloride, N-vinylcarbazole, vinylcyclohexene dioxide, 2-vinylpyridine, 4-vinylpyridine, N-vinylpyrrolidone, vinyl silane, vinylsulfonic acid, 4-vinyltoluene, and vinyltriethoxysilane. The polymer may comprise at least one monomer selected from the group consisting of acryloylmorpholine and N-isopropyl acrylamide.

An aspect of the invention is a method of using the enzyme-polymer solvent system. The system can be provided to a reaction. The enzyme and solvent can be determined by the reaction. The polymer can be a copolymer and can be selected such that one monomer of the copolymer is soluble (freely soluble, soluble or very soluble) in the solvent, while the second polymer is insoluble (insoluble, slightly soluble, or very insoluble) in the solvent. The system is soluble at the reaction temperature. In some embodiments, the system can be provided in excess.

An aspect of the invention is a method of recycling the enzyme-polymer. The method includes providing a solution comprising the enzyme-polymer, and then decreasing the temperature of the solution to below an upper critical solution temperature (UCST) or increasing the temperature of the solution to above a lower critical solution temperature (LCST) to form a precipitate comprising the enzyme. The precipitate can subsequently be filtered from the solvent and recycled.

In some embodiments, the recycled enzyme-polymer can have a catalytic activity that is at least about 75% of the catalytic activity of a non-recycled enzyme-polymer. In some embodiments, the catalytic activity can be between 75% and about 100% of a non-recycled enzyme-polymer.

In some embodiments, the polymer can be selected such that the transition point between a soluble and insoluble polymer in the system is near (within about 50 degrees, in some embodiments between about 10 degrees and about 50 degrees) of the reaction temperature. In some embodiments, the cloud temperature range can be between about 4° C. and about 78° C.

Various modifications of the above-described invention will be evident to those skilled in the art. It is intended that such modifications are included within the scope of the following claims.

The invention is illustrated by the following non-limiting Examples.

Example 1

LipA expression was induced via addition of isopropyl β-D-1-thiogalactopyranoside (IPTG) to BL21 DE3 *Escherichia coli* cells that harbored the gene for LipA in a pET-21B plasmid. Upon expression of LipA, the enzyme was purified from crude lysate using a $Ni^{2+}$-charged Bio-Scale Mini cartridge. The concentration of the resulting purified LipA was quantified using the bicinchoninic acid assay.

A number of N-hydroxysuccinimide ester (NHS)-terminated PAN polymers were synthesized by reversible addition-fragmentation chain-transfer polymerization (RAFT), as illustrated in FIG. 1, where x and y represent the number of AcMO units and NIPAAm units, respectively, in the PAN polymer. The AcMO and NIPAAm monomers were purified before use, and copolymer compositions were controlled by varying the ratio of AcMO to NIPAAm in the reaction solution between 0.58 and 0.88, while keeping the total monomer concentration constant at 2 M in 1,4-dioxane; at NIPAAm mole fractions below 0.58 the cloud point of LipA-PAN is below the 4° C. detection limit, and at NIPAAm mole fractions above 0.88 the cloud point is above the boiling point of ethanol (i.e. one of the transesterification substrates). The polymer molecular weight and polydispersity index (PDI) were kept constant or near-constant (44.4 to 55.7 kg/mol and less than 1.25, respectively) by maintaining the same ratios of total monomer to chain transfer agent and chain transfer agent to radical initiator. After polymerization, the products were precipitated into diethyl ether and analyzed by gel permeation chromatography (GPC) using an EcoSEC HLC 8320GPC and poly(methyl methacrylate) (PMMA) standards, and by $^1$H nuclear magnetic resonance (NMR) spectroscopy using a Bruker Avance III 300 MHz NMR spectrometer.

The apparent molecular weights and PDI values of the polymers are given in Table 1. All values are approximate.

TABLE 1

Characterization of PAN used in the preparation of LipA-PAN conjugates

| Sample ID | NIPAAm mole fraction | Polymer $M_n$ (kg/mol) | PDI |
|---|---|---|---|
| PAN-58 | 0.583 | 55.3 | 1.22 |
| PAN-61 | 0.614 | 54.5 | 1.20 |
| PAN-62 | 0.623 | 55.7 | 1.20 |
| PAN-63 | 0.630 | 54.2 | 1.15 |
| PAN-65 | 0.651 | 52.2 | 1.18 |
| PAN-68 | 0.679 | 54.4 | 1.21 |
| PAN-72 | 0.723 | 55.2 | 1.24 |
| PAN-76 | 0.759 | 52.8 | 1.18 |
| PAN-77 | 0.774 | 54.0 | 1.24 |
| PAN-78 | 0.783 | 53.3 | 1.15 |
| PAN-79 | 0.790 | 55.4 | 1.21 |
| PAN-80 | 0.801 | 52.4 | 1.17 |
| PAN-82 | 0.824 | 52.5 | 1.11 |
| PAN-86 | 0.860 | 45.8 | 1.18 |
| PAN-87 | 0.872 | 44.4 | 1.14 |
| PAN-88 | 0.882 | 46.4 | 1.25 |

Figure 2:
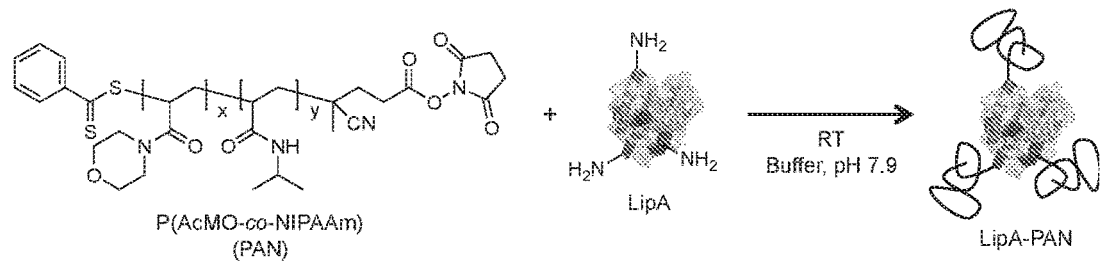
FIG. 2 is an illustration of a scheme for conjugation of the NETS-terminated PAN polymers synthesized by the method illustrated in FIG. 1 to unmodified lipase ("LipA") by NETS-amine coupling.

LipA-PAN conjugates were prepared by reacting the terminal NHS group on the PAN polymers with free amines on the surface of LipA, as illustrated in FIG. 2, in aqueous buffer (3 vol % glycerol, 200 mM sodium chloride, 50 mM sodium phosphate; pH 7.9) for one hour at room temperature with 100 rpm mixing on a shaking table incubator. Analysis of the crystal structure of LipA by Swiss-PDB Viewer revealed that although there are a total of twelve total amines (eleven primary amines from lysine residues, plus the N-terminal amine) in the primary sequence of the enzyme, only seven have greater than 30% of their surface area accessible to the solvent.

For the preparation of all conjugates, a 20:1 molar ratio of the polymer to the primary amines in the enzyme was used. Immediately following reaction, the LipA-PAN conjugates were passed over an $Ni^{2+}$-charged Bio-Scale Mini cartridge to remove any remaining free (i.e. unattached to the enzyme) polymer. The average number of polymers per enzyme was determined, using the 2,4,6-trinitrobenzene sulfonic acid (TNBSA) assay, to be between 2.3 and 3.7, and the average number of attached polymer chains and the molecular weight of the polymer was used in turn to estimate the total theoretical molecular weight of each conjugate, as illustrated in Table 2 below. All values in Table 2 are approximate.

| Sample ID | Polymers per enzyme | Theoretical total molecular weight (kDa) |
| --- | --- | --- |
| LipA-PAN58 | 3.6 ± 0.2 | 220 ± 10 |
| LipA-PAN61 | 3.2 ± 0.3 | 190 ± 20 |
| LipA-PAN62 | 3.3 ± 0.4 | 200 ± 20 |
| LipA-PAN63 | 2.9 ± 0.1 | 180 ± 10 |
| LipA-PAN65 | 3.0 ± 0.1 | 180 ± 10 |
| LipA-PAN68 | 2.9 ± 0.1 | 180 ± 10 |
| LipA-PAN72 | 2.9 ± 0.4 | 180 ± 20 |
| LipA-PAN76 | 2.8 ± 0.4 | 170 ± 20 |
| LipA-PAN77 | 3.0 ± 0.4 | 180 ± 20 |
| LipA-PAN78 | 2.3 ± 0.1 | 140 ± 10 |
| LipA-PAN79 | 2.8 ± 0.5 | 180 ± 30 |
| LipA-PAN80 | 2.5 ± 0.2 | 150 ± 10 |
| LipA-PAN82 | 3.3 ± 0.4 | 190 ± 20 |
| LipA-PAN86 | 3.5 ± 0.6 | 180 ± 30 |
| LipA-PAN87 | 3.7 ± 0.6 | 180 ± 30 |
| LipA-PAN88 | 3.5 ± 0.2 | 180 ± 10 |

The concentration of enzyme for the conjugates was similarly determined using the bicinchoninic acid assay, which was insensitive to the presence of free PAN in solution. Sodium dodecyl sulfate polyacrylamide gel electrophoresis (SDS-PAGE) analysis was performed under denaturing and reducing conditions on a 4-15% acrylamide gradient gel using Mini-PROTEAN® TGX™ Precast Gels with Coomassie staining.

Figure 3A:
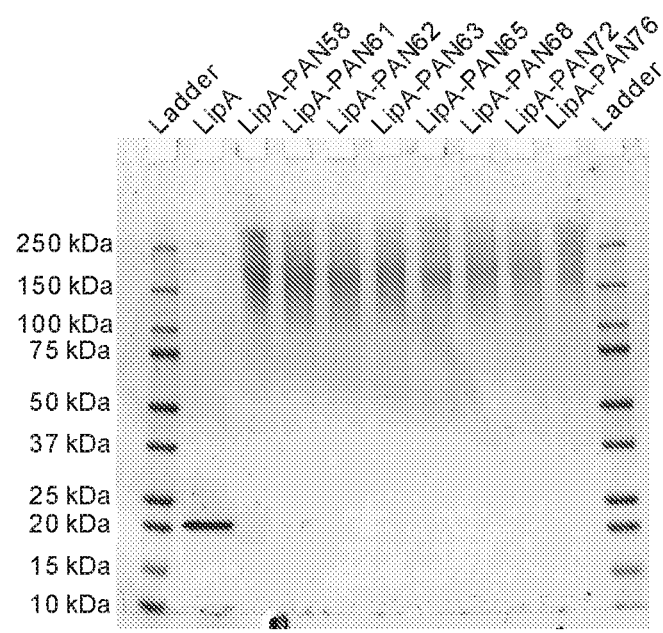
FIGS. 3A and 3B are sodium dodecyl sulfate polyacrylamide gel electrophoresis (SDS-PAGE) analyses of LipA and lipase-poly(acryloylmorpholine-ran-N-isopropyl acrylamide) ("LipA-PAN") conjugates.
Figure 3B:
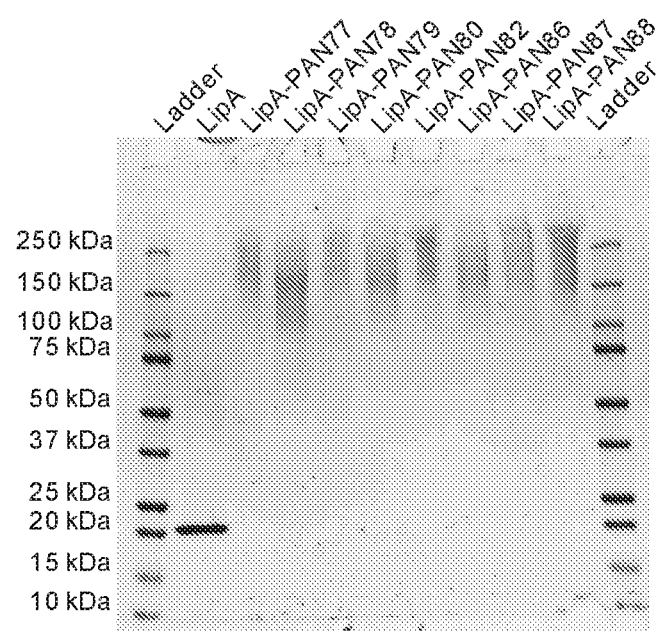

Notably, although the theoretical total molecular weight of the conjugates varied between 140 kDa and 220 kDa, the majority of conjugates had theoretical molecular weights between 170 kDa and 190 kDa. Given that the conjugates were of similar total size, differences in solubility and thus catalytic activity can be attributed primarily to the composition of the polymer. The extent of modification of each conjugate was confirmed by sodium dodecyl sulfate polyacrylamide gel electrophoresis (SDS-PAGE) analysis performed under denaturing and reducing conditions on a 4-15% acrylamide gradient gel using Mini-PROTEAN® TGX™ Precast Gels with Coomassie staining as illustrated in FIGS. 3A and 3B. Virtually 100% of the LipA was modified for each conjugate. The SDS-PAGE analysis further confirmed that the total theoretical molecular weight of the conjugates was broadly similar, as evident by the location of the bands in each lane.

As FIGS. 3A and 3B further illustrate, the LipA used for modification was more than 95% pure, as determined by densitometry of the lane with unmodified LipA. Additionally, based on analysis of solvent accessibility, amines on the side chains of Lys44, Lys61, Lys69, Lys88, and Lys112 were the most likely to be modified; these sites, which have solvent accessibilities of at least about 50%, are randomly distributed around the surface of the enzyme, rather than concentrated on one face. The N-terminal α-amino group is also presumably highly accessible and thus reactive, because the N-terminus of LipA protrudes outwardly from the enzyme. However, given that the polymer chains are significantly larger (about 2.5 times, by mass) than the enzyme, it is likely that the polymer chains can wrap around the enzyme, and it is therefore not to be expected that the location of attachment of the polymer plays a significant role in the solubility behavior of the enzyme-polymer conjugates.

Example 2

The thermodynamic favorability of copolymer-IL interactions is made highly sensitive to temperature by introducing NIPAAm into AcMO polymers to form PAN copolymers. In [BMIM][PF$_6$], PAN has UCST-type behavior, i.e. the polymer is soluble at temperatures above the cloud point and insoluble at temperatures below the cloud point. Because the cloud point is dependent on the composition of the copolymer, varying the ratio of AcMO units to NIPAAm units provides a simple method for tuning the cloud point of PAN in [BMIM][PF$_6$]. As such, the total thermodynamic favorability of the interactions between the LipA-PAN conjugates and [BMIM][PF$_6$] are also highly temperature-dependent; specifically, the present inventors have found that modification of LipA with PAN facilitates dissolution of LipA above the cloud point of the conjugate and separation of LipA below the cloud point.

The initial rate of transesterification of 100 mM nitrophenyl butyrate with 1 M ethanol in [BMIM][PF$_6$], as catalyzed by the LipA-PAN61 conjugate of Example 1, was assayed spectrophotometrically by monitoring the release of 4-nitrophenol at 420 nm in 96-well plates using an Infinite M Plex plate reader at 40° C. For activity measurements, freeze-dried LipA-PAN61, which was lyophilized from a 5 mM sodium phosphate buffer (pH 8.0) was used. LipA-PAN61 conjugate was first dissolved in the ionic liquid (IL) at a concentration equivalent to 1 mg/mL of enzyme by vigorously mixing the lyophilized powder in the IL solution at 95° C. for three minutes on a heat block. Samples were then diluted to a final concentration equivalent to 0.25 mg/mL of enzyme before measuring the activity.

For activity measurements involving the cycling of the conjugate between the dissolved state and the precipitated state, LipA-PAN61 was dissolved at a concentration equivalent to 1 mg/mL of enzyme in [BMIM][PF$_6$] as described above. Stock solutions were cooled to 40° C., and aliquots were diluted to an equivalent of 0.25 mg/mL of enzyme for measurement of initial (cycle 0) activity at 40° C. The stock solutions were then cooled to 4° C. for five minutes to precipitate the LipA-PAN61 conjugate, and subsequently heated back to 40° C. and incubated for five minutes to re-dissolve the LipA-PAN61 conjugate. Upon redissolution, the conjugate was diluted to an equivalent of 0.25 mg/mL of enzyme and assayed at 40° C., as described above. The process of cycling the conjugate between the dissolved state and the precipitated state was repeated a maximum of ten times.

Figure 4A:
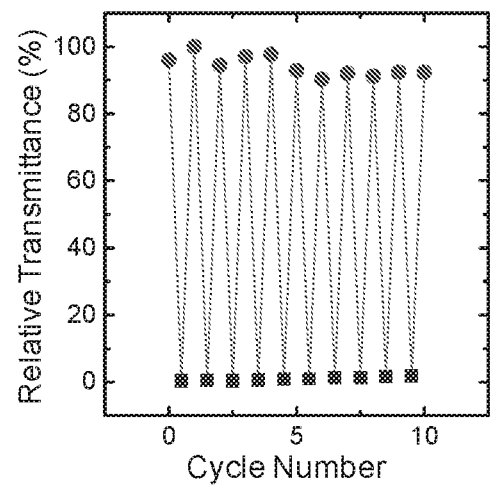
FIG. 4A illustrates relative transmittance as a function of precipitation cycling of a LipA-PAN conjugate at a 1 mg/mL enzyme concentration in 1-butyl-3-methylimidazolium hexafluorophosphate ("[BMIM][PF$_6$]") containing 1 M ethanol.

Referring now to FIG. 4A, data points illustrated as circles represent the relative transmittance of the LipA-PAN61 conjugate at 40° C. (above the cloud point), and data points illustrated as squares represent the relative transmittance of the LipA-PAN61 conjugate at 4° C. (at which temperature the conjugate is insoluble). Cycle number represents the number of times the temperature was switched from 40° C. to 4° C. and back to 40° C.; cycle 0 represents relative transmittance at 40° C. before cooling to 4° C. for the first time, i.e. before the first precipitation of the conjugate from the IL).

Figure 4B:
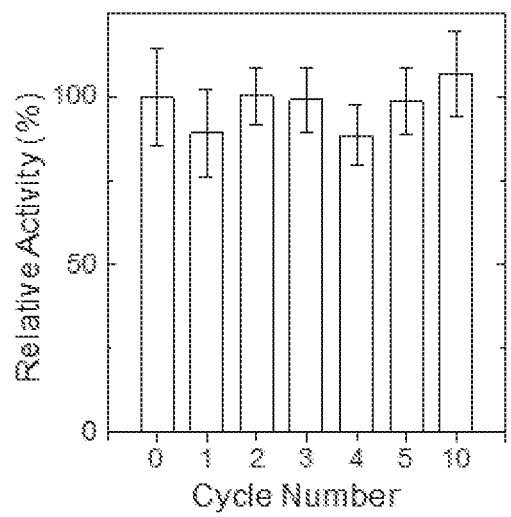
FIG. 4B illustrates initial rate activity for the transesterification of 4-nitrophenyl butyrate with ethanol, catalyzed by a LipA-PAN conjugate, as a function of cycle number.

Referring now to FIG. 4B, initial rate activity for the transesterification of 0.1 M 4-nitrophenyl butyrate with 1 M ethanol, catalyzed by LipA-PAN61, is illustrated as a function of cycle number. Transesterification activity was normalized such that the apparent activity for cycle 0 is represented as 100%. Error bars represent one standard deviation across at least four distinct experiments.

LipA-PAN conjugates display a UCST-type phase behavior in the IL, which is evident by repeatedly dissolving and precipitating the conjugates in the IL; LipA-PAN61 was chosen as exemplary because it has a convenient cloud point of 20° C. When initially heated to 40° C., the relative transmittance of the conjugate in the IL is approximately 100%, as illustrated in FIG. 4A, which indicates that the conjugate is almost completely dissolved; after cooling to 4° C., the relative transmittance of the conjugate is approximately 0% due to precipitation of the conjugate. Importantly, even after ten cycles, the relative transmittances at 40° C. and 4° C. are unchanged, suggesting that the process is completely reversible, i.e. that all of the precipitate is readily re-dissolved upon heating. The relative transmittance of LipA-PAN61 in [BMIM][PF$_6$] in these experiments was measured in the presence of 1 M ethanol, which is advantageous because ethanol is a transesterification substrate for LipA.

As illustrated in FIG. 4B, the conjugate remarkably retains essentially all of its catalytic activity even after ten cycles. Given that LipA-PAN61 appears not to lose any catalytic activity between cycles, it may be concluded that any unfolding of the enzyme due to precipitation at 4° C. is fully reversible. Additionally, the activity of the residual soluble conjugate in the IL after precipitation, as measured by removing the precipitated conjugate by centrifugation and assaying the activity of the remaining soluble conjugate at 40° C., is just 7% of the initial activity of the dissolved conjugate, confirming that very little of the conjugate remains soluble after cooling. Also noteworthy is the fact that the activity of the LipA-PAN61 in catalyzing transesterification at 40° C. is 21±2 times greater than the activity of unmodified LipA in anhydrous [BMIM][PF$_6$].

Example 3

To determine the extent to which the cloud point of LipA-PAN conjugates can be tuned, the cloud points of the LipA-PAN conjugates of Example 1 were determined by measuring the transmittance at 658 nm as a function of temperature using a Litesizer 500. Measurements of the cloud point were obtained in aqueous buffer (5 mM sodium phosphate; pH 8.0) and [BMIM][PF$_6$] with or without 1 M ethanol, at a concentration equivalent to 1 mg/mL of enzyme. The raw transmittance values over the range of temperatures analyzed were fit to a sigmoidal function of the form $$F(X) = A_1 + \frac{(A_2 - A_1)}{1 + e^{\left(\frac{X - X_0}{dX}\right)}},$$

where $A_1$, $A_2$, X, $X_0$, and dX represent the minimum transmittance value, maximum transmittance value, mole fraction of NIPAAm, mole fraction of NIPAAm at the inflection point of the sigmoid, and a constant related to the width of the sigmoid, respectively. The cloud point of the LipA-PAN conjugate was defined as the temperature at the inflection point of the sigmoid ($T_0$).

Figure 5A:
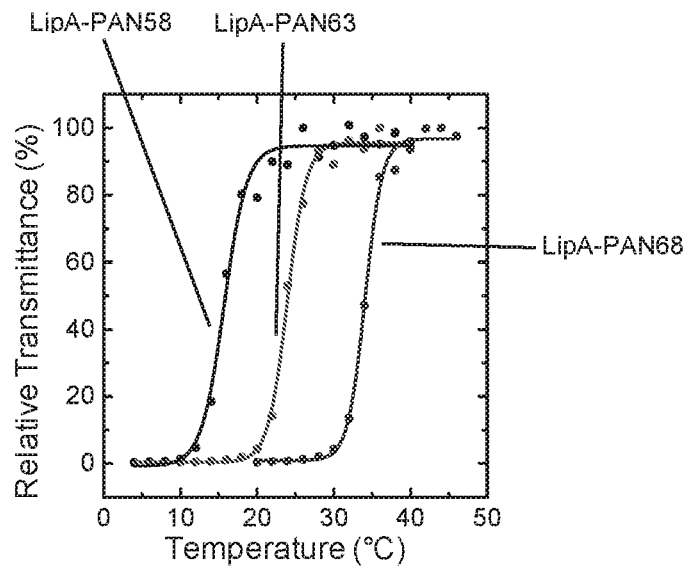
FIG. 5A illustrates cloud point curves for three LipA-PAN conjugates in [BMIM][PF$_6$] containing 1 M ethanol.
Figure 5B:
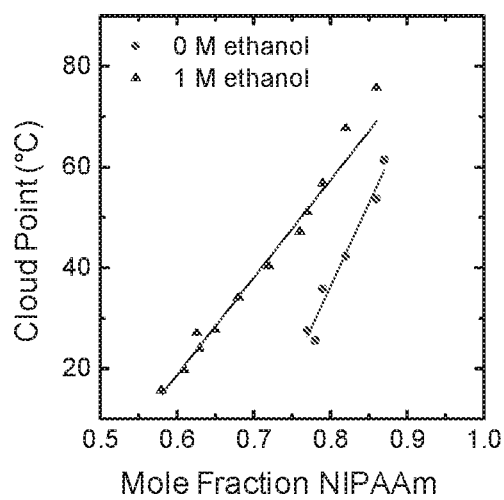
FIG. 5B illustrates the dependence of LipA-PAN cloud point on the mole fraction of N-isopropyl acrylamide (NIPAAm) in the poly(acryloylmorpholine-ran-N-isopropyl acrylamide) ("PAN").

FIG. 5A illustrates cloud point data for three representative samples: LipA-PAN58 (leftmost curve), LipA-PAN63 (middle curve), and LipA-PAN68 (rightmost curve). Analysis of the cloud points shows that, for the range of mole fractions of NIPAAm used in preparing PAN, the cloud point in [BMIM][PF$_6$] varies between 16° C. and 76° C., as illustrated in FIG. 5B. Notably, the cloud point is linearly dependent on the mole fraction of NIPAAm in the LipA-PAN conjugates over the relevant range of NIPAAm mole fractions (0.58 to 0.88). Given the linearity of the trend, the composition of the PAN copolymer for use in the enzyme-polymer conjugates of the present invention can easily be altered to yield a desired cloud point. The present inventors have also contemplated that the use of block, rather than random, copolymers may be another parameter in controlling solubility behavior, and the use of block rather than random copolymers in enzyme-polymer conjugates is within the scope of the present invention.

Also of note is the fact that the relationship between cloud point and the mole fraction of NIPAAm is affected by the presence of ethanol, as represented by the data points illustrated as triangles in FIG. 5B. Specifically, in the presence of 1 M ethanol, the cloud point increases by 10 to 25° C., and the slope of the relationship is reduced (i.e. the cloud point is less sensitive to polymer composition). Imidazolium-type ILs are known to have highly complex hydrogen bonding networks that significantly impact the physical and chemical properties of the IL, and lower critical solution temperature (LCST)-type behavior of poly(NIPAAm) in water is known to be the result of a balance between favorable hydrogen bonding of the amide group with water and unfavorable interactions between the hydrophobic isopropyl group and water. Therefore, without wishing to be bound by any particular theory, it is believed that, for PAN polymers in ILs, hydrogen bonding between the imidazolium IL and the amide group of the NIPAAm units and/or the cyclic ether of the AcMO units favors solubility, whereas interactions with the isopropyl group disrupt the IL structure and hydrogen bonding and thus disfavor solubility at low temperatures.

In the compositions of the present invention, the behavior of the conjugate/IL solution may be complex as a result of the diverse molecular-level interactions between the copolymer units, LipA (or other enzyme), and the IL solvent. Additives, including ethanol or other reaction substrates, may also change the effective solvent quality and further complicate the system by introducing additional interactions, including new hydrogen bonds of different strengths and temperature dependence. Without wishing to be bound by any particular theory, it is believed that, for LipA-PAN conjugates in [BMIM][PF$_6$], the interactions of the AcMO with the IL are significantly more favorable than the NIPAAm interactions with the IL and thus drive the conjugate solubility; the inclusion of ethanol differentially modulates the strength of these interactions, such that the difference in favorability is reduced (but the AcMO interactions remain more favorable than the NIPAAm interactions). It is possible that the addition of 4-nitrophenyl butyrate may also affect the conjugate cloud point. Based on these and other factors, it is critical for those of skill in the art to consider how other substrates, including other alcohols, may impact the solubility behavior of the enzyme-polymer conjugate for a given reaction.

Example 4

The extraction of the LipA-PAN61 conjugate of Example 1 from [BMIM][PF$_6$] to aqueous buffer was measured by initially dissolving an equivalent of 1 mg/mL of enzyme in [BMIM][PF$_6$]. As indicated above, the dissolution of the conjugate at these conditions was facilitated by vigorously mixing the conjugate solution at 95° C. for three minutes. After mixing and cooling to 40° C., 1 M ethanol was added to the conjugate-containing IL solution to mimic the conditions used for activity measurements. The IL solution containing the conjugate and ethanol was subsequently mixed with buffer (5 mM sodium phosphate; pH 8.0) at a 1:10 volume ratio of IL solution to buffer for one minute. Prior to extraction, the IL solution and the buffer were pre-equilibrated separately at the temperature at which the LipA-PAN61 was extracted, which varied between 10° C. and 60° C. The biphasic IL-aqueous mixture was settled by centrifugation at 2000 g for 30 seconds to achieve rapid phase separation. The extraction efficiency was defined as the percentage of LipA-PAN61 recovered in the aqueous phase after mixing. The concentration of the conjugate in the buffer was determined using the bicinchoninic acid assay, which was unaffected by the presence of trace amounts of [BMIM][PF$_6$].

Figure 6A:
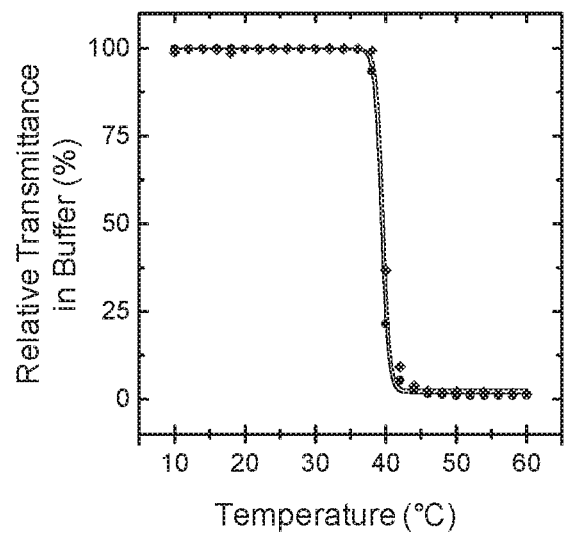
FIG. 6A illustrates relative transmittance of a LipA-PAN conjugate in aqueous buffer, with (circles) and without (diamonds) ethanol, as a function of temperature.
Figure 6B:
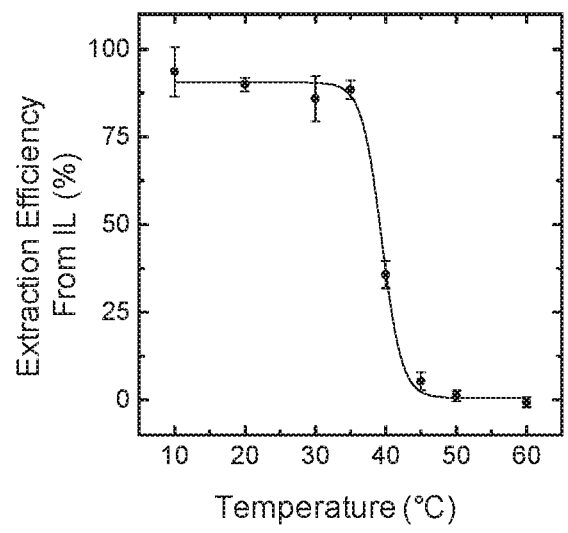
FIG. 6B illustrates extraction efficiency of a LipA-PAN conjugate from [BMIM][PF$_6$] containing 1 M ethanol into aqueous buffer, as a function of temperature.

The extraction efficiency shows a strong temperature-dependence, as illustrated in FIG. 6B; notably, the extraction efficiency is greater than 90% at low temperatures but drops precipitously at about 40° C. and is near zero at temperatures at or above 45° C. The solid lines in FIGS. 6A and 6B represent sigmoidal fits of the data; error bars represent one standard deviation across at least three distinct trials.

Over the temperature range investigated by the present inventors, PAN exhibits a UCST-type behavior in [BMIM][PF$_6$] but an LCST-type behavior in aqueous solutions, due to the presence of the NIPAAm units. As FIG. 6A illustrates, this LCST-type behavior has the result that the LipA-PAN61 conjugate is soluble in buffer at temperatures below the cloud point of 39° C. but phase-separates at temperatures above the cloud point (as reflected by a decrease in optical transmission). Given the LCST-type behavior in buffer and the UCST-type behavior in IL, and more generally that the overall thermodynamic favorability of each solvent for LipA-PAN is highly temperature-sensitive, it is possible to selectively exchange LipA-PAN conjugates between solvents in a thermoreversible manner.

As this Example shows, LipA-PAN61 has a cloud point of 20° C. in the IL phase, i.e. [BMIM][PF$_6$] with 1 M ethanol, and a cloud point of 39° C. in the buffer. At temperatures below 20° C. the conjugate is insoluble in the IL phase and partitions completely into the aqueous phase in which it is soluble, and at temperatures above 39° C. the conjugate is insoluble in the aqueous phase and remains in the IL phase in which it is soluble; these disparate responses explain the transition between high and low extraction efficiencies into the buffer that are illustrated in FIG. 6B. At temperatures between 20° C. and 39° C., however, the conjugate is soluble in both phases, and partial segregation of the conjugate may be anticipated. Importantly, however, a high extraction efficiency was observed in this temperature range, suggesting that the interactions between LipA-PAN and water are more thermodynamically favorable than the interactions between LipA-PAN and [BMIM][PF$_6$]. The temperature dependence of the extraction efficiency is thus primarily dictated by the LCST-type behavior of the conjugates in buffer, and the inflection point in the extraction efficiency curve corresponds to the aqueous cloud point.

Ethanol, which was initially present in the IL phase at a concentration of 1 M, may partition between the aqueous and IL phases during mixing. Transfer of the ethanol out of the IL phase lowers the UCST-type cloud point of the conjugate in IL, but may also impact the LCST-type cloud point in the aqueous phase. The aqueous cloud point was measured in buffer containing 0.1 M ethanol; the presence of this quantity of ethanol had a negligible effect (less than 1° C.) on the aqueous cloud point, indicating that the thermoresponsive extraction behavior is insensitive to the presence of ethanol in the system.

Figure 7:
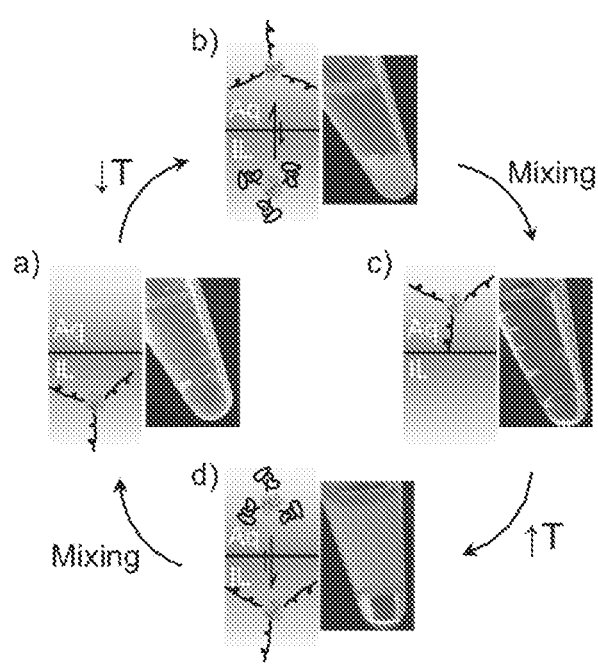
FIG. 7 is a generalized schematic illustrating thermoreversible shuttling of a LipA-PAN conjugate between [BMIM][PF$_6$] and aqueous solutions.

To demonstrate the temperature-dependent shuttling of LipA between [BMIM][PF$_6$] and aqueous buffer, LipA-PAN61 at a concentration equivalent to 1 mg/mL of enzyme was initially dissolved in [BMIM][PF$_6$] containing 1 M ethanol. Sodium phosphate buffer (5 mM; pH 8.0) was added to the conjugate-containing IL solution at a 1:10 volume ratio of IL solution to buffer; this immiscible system was equilibrated at 45° C., as illustrated in step (a) of FIG. 7. The IL/buffer mixture was then cooled to 4° C., whereupon the conjugate became insoluble in the IL phase and caused the IL phase to appear cloudy, as illustrated in step (b) of FIG. 7. Upon mixing to extract the precipitated LipA-PAN61 into the aqueous phase, both phases once again become transparent, as illustrated in step (c) of FIG. 7. Finally, when the biphasic system is reheated to 45° C., the conjugate becomes insoluble in the aqueous phase and can be selectively extracted back into the IL phase, as illustrated in step (d) of FIG. 7, thereby completing the thermoresponsive shuttling cycle.

Embodiments of the present invention may be extended to other enzyme/solvent systems, and such embodiments are within the scope of the present invention. By way of non-limiting example, the methods and systems described herein may readily be used to recycle enzymes from other ILs (e.g. [BMIM][BF$_4$], [BMIM][NTf$_2$], [BMPy][Ntf$_2$], etc.), as well as a broad range of organic solvents commonly used for non-aqueous biocatalysis, such as hexane and acetonitrile. In addition to facilitating enzyme recycling, the thermoresponsive shuttling aspect of the present invention may also be used as a switch to activate or deactivate enzymes in a particular phase. Enzymes and other proteins that are modified with polymers to exhibit UCST and/or LCST behavior may also have utility as surfactants for transferring protein cargoes between immiscible solvents. The reversible assembly of proteins into hierarchical three-dimensional nanostructures by modulating the solubility of the protein in a solvent in response to changes in temperature may also be controlled by methods and systems of the present invention. Further applications include modifying enzymes or other proteins with polymers that are responsive to parameters other than temperature (e.g. light, pH, ionic strength, etc.) to mediate the interaction of the protein with the solvent in response to different triggers.

Various modifications of the above described invention will be evident to those skilled in the art. It is intended that such modifications are included within the scope of the following claims.

Ranges have been discussed and used within the foregoing description. One skilled in the art would understand that any sub-range within the stated range would be suitable, as would any number within the broad range, without deviating from the invention.

Additionally, various features/components of one embodiment may be combined with features/components of another embodiment. For example, features/components of one embodiment can be combined with features/components of another embodiment or features/components of multiple embodiments. To avoid repetition, every different combination of features has not been described herein, but the different combinations are within the scope of this disclosure. Additionally, if details (including additives, properties, dimensions, etc.) about a feature or component are described with one embodiment or one figure, then those details can apply to similar features of components in other embodiments or other figures.

The foregoing description of the present invention, related to enzyme-polymer conjugates, methods of using and making the same, as well as methods to recycle the enzyme-polymer conjugate. This description has been presented for purposes of illustration and description. Furthermore, the description is not intended to limit the invention to the form disclosed herein. Consequently, variations and modifications commensurate with the above teachings, and the skill or knowledge of the relevant art, are within the scope of the present invention. The embodiment described hereinabove is further intended to explain the best mode known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

The invention claimed is:

1. A method for recyclably using an enzyme as a catalyst in a solvent, comprising:
   a) reacting the enzyme with a polymer to form an enzyme-polymer conjugate;
   b) dissolving the enzyme-polymer conjugate in the solvent to form a solution;
   c) performing a chemical reaction in the solution, wherein the enzyme-polymer conjugate catalyzes the chemical reaction; and
   d) extracting the enzyme-polymer conjugate from the solution,
   wherein a catalytic activity of the enzyme-polymer conjugate after step d) is at least about 75% of a catalytic activity of the enzyme-polymer conjugate before step c).

2. The method of claim 1, wherein the enzyme is lipase.

3. The method of claim 1, further comprising purifying the enzyme-polymer conjugate by a method selected from the group consisting of affinity chromatography, ammonium sulfate precipitation, dialysis, and size exclusion chromatography.

4. The method of claim 1, wherein the polymer is a copolymer.

5. The method of claim 4, wherein the polymer is a random copolymer.

6. The method of claim 4, wherein the copolymer comprises at least one monomer that is highly soluble, freely soluble, or soluble in the solvent and at least one monomer that is insoluble, poorly soluble, very slightly soluble, or slightly soluble in the solvent.

7. The method of claim 1, wherein the chemical reaction is selected from the group consisting of a transesterification reaction, an oxidation/reduction reaction, a group transfer reaction, a hydrolysis reaction, an isomerization reaction, and a dehydration reaction.

8. The method of claim 1, wherein step d) comprises changing a temperature of the solution to precipitate the enzyme-polymer conjugate.

9. The method of claim 1, wherein step d) comprises extracting the enzyme-polymer conjugate with an extractant.

10. The method of claim 9, wherein the enzyme-polymer conjugate exhibits upper critical solution temperature (UCST) behavior in the solvent and lower critical solution temperature (LCST) behavior in the extractant.

11. The method of claim 9, wherein the enzyme-polymer conjugate exhibits LCST behavior in the solvent and UCST behavior in the extractant.

* * * * *